(12) United States Patent
Nelson et al.

(10) Patent No.: US 7,553,828 B2
(45) Date of Patent: *Jun. 30, 2009

(54) 9-AMINOMETHYL SUBSTITUTED MINOCYCLINE COMPOUNDS

(75) Inventors: Mark L. Nelson, Norfolk, MA (US); Roger Frechette, Reading, MA (US); Mohamed Y. Ismail, Bedford, MA (US); Laura Honeyman, Roslindale, MA (US); Todd Bowser, Charlton, MA (US); Beena Bhatia, Arlington, MA (US)

(73) Assignee: Paratek Pharmaceuticals, Inc., Boston, MA (US)

( * ) Notice: Subject to any disclaimer, the term of this patent is extended or adjusted under 35 U.S.C. 154(b) by 358 days.

This patent is subject to a terminal disclaimer.

(21) Appl. No.: 10/786,881

(22) Filed: Feb. 24, 2004

(65) Prior Publication Data

US 2005/0026876 A1    Feb. 3, 2005

Related U.S. Application Data

(63) Continuation of application No. 10/412,656, filed on Apr. 10, 2003, now abandoned, which is a continuation-in-part of application No. 10/384,855, filed on Mar. 10, 2003, now abandoned, said application No. 10/412,656 is a continuation-in-part of application No. 09/895,857, filed on Jun. 29, 2001, now Pat. No. 6,846,939.

(60) Provisional application No. 60/395,495, filed on Jul. 12, 2002, provisional application No. 60/362,654, filed on Mar. 8, 2002, provisional application No. 60/275,621, filed on Mar. 13, 2001.

(51) Int. Cl.
*A61K 31/65* (2006.01)
*C07C 50/22* (2006.01)

(52) U.S. Cl. ..................................... 514/152; 552/205

(58) Field of Classification Search ................ 552/205, 552/203, 206; 514/152
See application file for complete search history.

(56) References Cited

U.S. PATENT DOCUMENTS

| | | | |
|---|---|---|---|
| 3,007,965 A | 11/1961 | Growich | |
| 3,226,436 A | 12/1965 | Petisi et al. | |
| RE26,253 E | 8/1967 | Petisi et al. | |
| 3,338,963 A | 8/1967 | Petisi et al. | |
| RE26,271 E | 9/1967 | Boothe et al. | |
| 3,341,585 A | 9/1967 | Bitha et al. | |
| 3,345,379 A | 10/1967 | Martell, Jr. et al. | |
| 3,345,410 A | 10/1967 | Winterbottom | |
| 3,360,561 A | 12/1967 | Zambrano | |
| 3,373,193 A | 3/1968 | Schroeder et al. | |
| 3,397,230 A | 8/1968 | Winterbottom et al. | |
| 3,454,697 A | 7/1969 | Joyner et al. | |
| 3,483,251 A | 12/1969 | Zambrano | |
| 3,518,306 A | 6/1970 | Martell, Jr. | |
| 3,579,579 A | 5/1971 | Hlavka et al. | |
| 3,901,942 A | 8/1975 | Bernardi et al. | |
| 4,018,889 A | 4/1977 | Armstrong | |
| 4,024,272 A | 5/1977 | Rogalski et al. | |
| 4,126,680 A | 11/1978 | Armstrong | |
| 5,248,797 A | 9/1993 | Sum | |
| 5,281,628 A | 1/1994 | Hlavka et al. | |
| 5,284,963 A | 2/1994 | Sum et al. | |
| 5,326,759 A | 7/1994 | Hlavka et al. | |
| 5,328,902 A | 7/1994 | Sum et al. | |
| 5,371,076 A | 12/1994 | Lee et al. | |
| 5,380,888 A | 1/1995 | Sum et al. | |
| 5,386,041 A | 1/1995 | Sum et al. | |
| 5,401,729 A | 3/1995 | Sum et al. | |
| 5,401,863 A | 3/1995 | Hlavka et al. | |
| 5,420,272 A | 5/1995 | Sum et al. | |
| 5,430,162 A | 7/1995 | Sum et al. | |
| 5,442,059 A | 8/1995 | Sum et al. | |
| 5,457,096 A | 10/1995 | Sum et al. | |
| 5,466,684 A | 11/1995 | Sum et al. | |
| 5,494,903 A | 2/1996 | Hlavka et al. | |
| 5,495,018 A | 2/1996 | Sum et al. | |
| 5,495,030 A | 2/1996 | Sum et al. | |
| 5,495,031 A | 2/1996 | Sum et al. | |

(Continued)

FOREIGN PATENT DOCUMENTS

EP    535346 B1    4/1993

(Continued)

OTHER PUBLICATIONS

Baldini, M., et al. "Diazo derivatives of amino acids and peptides as possible antineoplastic chemotherapeutic agents. 1. General considerations and methods." *Boll Soc Ital Biol Sper.* Jun. 30, 1960; 36:577-81.

(Continued)

*Primary Examiner*—Sabiha N. Qazi
(74) *Attorney, Agent, or Firm*—McCarter & English, LLP; Elizabeth A. Hanley, Esq.; Meaghan L. Richmond

(57) ABSTRACT

The present invention pertains, at least in part, to novel 9-substituted minocycline compounds. These minocycline compounds can be used to treat numerous tetracycline compound-responsive states, such as bacterial infections and neoplasms, as well as other known applications for minocycline and minocycline compounds in general, such as blocking tetracycline efflux and modulation of gene expression.

4 Claims, No Drawings

U.S. PATENT DOCUMENTS

| | | | |
|---|---|---|---|
| 5,512,553 | A | 4/1996 | Sum et al. |
| 5,529,990 | A | 6/1996 | Hlavka et al. |
| 5,530,117 | A | 6/1996 | Hlavka et al. |
| 5,567,692 | A | 10/1996 | Sum et al. |
| 5,574,026 | A | 11/1996 | Backer et al. |
| 5,639,742 | A | 6/1997 | Lee et al. |
| 5,675,030 | A | 10/1997 | Krishnan et al. |
| 5,834,450 | A | 11/1998 | Su |
| 5,843,925 | A | 12/1998 | Backer et al. |
| 5,856,315 | A | 1/1999 | Backer et al. |
| 5,886,175 | A | 3/1999 | Sum et al. |
| 6,500,812 | B2 | 12/2002 | Nelson et al. |
| 6,506,740 | B1 | 1/2003 | Ashley et al. |
| 6,617,318 | B1 | 9/2003 | Nelson et al. |
| 6,624,168 | B2 | 9/2003 | Nelson et al. |
| 6,642,270 | B2 | 11/2003 | Nelson et al. |
| 6,683,068 | B2 | 1/2004 | Nelson et al. |
| 6,818,634 | B2 | 11/2004 | Nelson et al. |
| 6,818,635 | B2 | 11/2004 | Nelson et al. |
| 6,833,365 | B2 | 12/2004 | Levy et al. |
| 6,841,546 | B2 | 1/2005 | Draper et al. |
| 6,846,939 | B2 * | 1/2005 | Nelson et al. ............ 552/205 |
| 7,001,918 | B2 | 2/2006 | Huss et al. |
| 7,045,507 | B2 * | 5/2006 | Draper et al. ............ 514/31 |
| 7,056,902 | B2 | 6/2006 | Nelson et al. |
| 7,067,681 | B2 | 6/2006 | Nelson et al. |
| 7,094,806 | B2 | 8/2006 | Nelson |
| 2002/0103171 | A1 | 8/2002 | Nelson et al. |
| 2002/0111335 | A1 | 8/2002 | Nelson et al. |
| 2002/0115644 | A1 | 8/2002 | Levy et al. |
| 2002/0193354 | A1 | 12/2002 | Nelson et al. |
| 2003/0100017 | A1 | 5/2003 | Draper et al. |
| 2003/0125348 | A1 | 7/2003 | Nelson et al. |
| 2003/0166585 | A1 | 9/2003 | Draper et al. |
| 2004/0033996 | A1 | 2/2004 | Nelson et al. |
| 2004/0048835 | A1 | 3/2004 | Nelson et al. |
| 2004/0063674 | A1 | 4/2004 | Levy et al. |
| 2004/0092490 | A1 | 5/2004 | Draper et al. |
| 2004/0138183 | A1 | 7/2004 | Nelson et al. |
| 2004/0152674 | A1 | 8/2004 | Levy et al. |
| 2004/0157806 | A1 | 8/2004 | Nelson et al. |
| 2004/0176334 | A1 | 9/2004 | Nelson et al. |
| 2004/0192657 | A1 | 9/2004 | Garcia-Luzón et al. |
| 2004/0214800 | A1 | 10/2004 | Levy et al. |
| 2004/0214801 | A1 | 10/2004 | Nelson et al. |
| 2004/0242548 | A1 | 12/2004 | Draper et al. |
| 2004/0266740 | A1 | 12/2004 | Huss et al. |
| 2005/0020545 | A1 | 1/2005 | Draper et al. |
| 2005/0026875 | A1 | 2/2005 | Nelson et al. |
| 2005/0038002 | A1 | 2/2005 | Nelson et al. |
| 2005/0137174 | A1 | 6/2005 | Ohemeng et al. |
| 2005/0143352 | A1 | 6/2005 | Nelson et al. |
| 2005/0187198 | A1 | 8/2005 | Nelson et al. |
| 2005/0215532 | A1 | 9/2005 | Levy et al. |
| 2005/0250744 | A1 | 11/2005 | Levy et al. |
| 2005/0282787 | A1 | 12/2005 | Myers et al. |
| 2006/0084634 | A1 | 4/2006 | Huss et al. |
| 2006/0089336 | A1 | 4/2006 | Nelson et al. |
| 2006/0160799 | A1 | 7/2006 | Alekshun |
| 2006/0166944 | A1 | 7/2006 | Berniac |
| 2006/0166945 | A1 | 7/2006 | Abato |
| 2006/0194773 | A1 | 8/2006 | Levy |

FOREIGN PATENT DOCUMENTS

| | | |
|---|---|---|
| EP | 536515 B1 | 4/1993 |
| EP | 582788 A1 | 2/1994 |
| EP | 582789 A1 | 2/1994 |
| EP | 582790 B1 | 2/1994 |
| EP | 582810 B1 | 2/1994 |
| EP | 582829 A1 | 2/1994 |
| EP | 618190 A1 | 10/1994 |
| GB | 921252 | 3/1963 |
| GB | 955766 | 4/1964 |
| WO | WO-95/22529 | 8/1995 |
| WO | WO 95/22529 A1 | 8/1995 |
| WO | WO 96/34852 A1 | 11/1996 |
| WO | WO 00/28983 A1 | 5/2000 |
| WO | WO 01/19784 A1 | 3/2001 |
| WO | WO 01/74761 A1 | 10/2001 |
| WO | WO 01/87823 A1 | 11/2001 |
| WO | WO 02/04406 A2 | 1/2002 |
| WO | WO 02/04406 A3 | 1/2002 |
| WO | WO 02/04407 A2 | 1/2002 |
| WO | WO 02/04407 A3 | 1/2002 |
| WO | WO 02/072022 A2 | 9/2002 |
| WO | WO 02/072031 A2 | 9/2002 |

OTHER PUBLICATIONS

Branceni, D., et al. "Use of tetracycline for the demonstration of the phenomena of extra-osseous calcification." *C.R. Seances Soc Biol Fil.* 1961; 155:1469-72.

Cope, et al. N,N-Dimethylcyclohexylmethylamine. *Org. Syn. Coll.* vol. 4. 1963; 339-44.

*Federal Register*. 1962; 27:3851.

Garrod, L.P. "Recent developments in antibiotic therapy." *Recenti Prog Med*. Jan. 1962; 32:3-24.

Genazzini, E., et al. *Atti. Soc. Ital. Sci. Vet*. 1964; 18:175-8.

Good, W. "The inhibition of haemolysis by phloridzin." *Biochim Biophys Acta*. Jan. 29, 1962; 56:359-61.

Hajdu, P. *Arzneimittel-Forsch*. 1962; 12:206-7.

Lucier, et al. N-Methylbutylamine. *Org. Syn. Coll.* vol. 5. 1973; 736.

Maniar, A., et al. "One of the factors influencing the action of antibiotics." *Ann Inst Pasteur* (Paris). Dec. 1961; 101:887-97.

Martell, et al. *J. Med. Chem*. 1967; 10(3);359-63.

Ritzerfeld, W., et al. "In vitro studies on 2 old and 2 new tetracycline preparations." *Arzneimittelforschung*. Jan. 1962; 12:30-2.

Roe, et al. Fatty Acid Amides: I. Preparation of Amides of Oleic and the 9,10-Dihydroxystearic Acids. *J. Am. Chem. Soc*. 71. 1949; 2215-18.

Spezial, et al. N,N-Diethyl-1,2,2-Trichlorovinylamine. *Org. Syn. Coll.* vol. 5. 1973; 387.

Stevens, et al. Studies on the Synthesis of Vitamin $B_{12}$. *J. Am. Chem. Soc*. 108. 1986; 1039-1049.

Strel'nokov. Effect of Tetracyclines on the Heart in Experiments by the Data of Electrocardiograms. *Antibiotiki*. 1965; 10(7):650-6.

van den Bogert, et al. "Doxycycline in combination chemotherapy of a rat leukemia." *Cancer Res*. Dec. 1, 1988; 48(23):6686-90.

Barden, Timothy C. et al, "Glycylcyclines'. 3.9-AMinodoxycyclinecarboxamides," *J. Med. Chem.*, vol. 37:3205-3211 (1994).

Kaza, Darrell J. et al, "Synthesis and Biological Evaluation of 9-Substituted Tetracycline Derivatives," *Bioorganic & Medicinal Chemistry Letters*, vol. 12:2163-2165 (2002).

Petersen, P.J. et al, "in Vitro and In Vivo Antibacterial Activities of a Novel Glycylcycline, the 9-t-Butylglycylamido Derivative of Minocycline (GAR-936)," *Antimicrobial Agents and Chemotherapy*, vol. 43(4):738-744 (1999).

Sum, Pahik-Eng et al, "Synthesis and antibacterial activity of 9-substituted minocycline derivatives," *Bioorganic & Medicinal Chemistry Letters*, vol. 16:400-403 (2006).

Sum, Phaik-Eng et al, "Synthesis and Structure-Activity Relationship of Novel Glycylcycline Derivatives Leading to the Discovery of GAR-936," *Bioorganic & Medicinal Chemistry Letters*, vol. 9:1459-1462 (1999).

Sum, Phaik-Eng et al, "Glycylcyclines. 1. A New Generation of Potent Antibacterial Agents through Modification of 9-Animotetracyclines," *J. Med. Chem.*, vol. 37:184-188 (1994).

International Search Report for Application No. PCT/US04/11242, Jan. 31, 2005.

* cited by examiner

9-AMINOMETHYL SUBSTITUTED MINOCYCLINE COMPOUNDS

RELATED APPLICATIONS

This application claims priority to U.S. patent application Ser. No. 10/412,656, filed on Apr. 10, 2003, which claims priority to Ser. No. 10/384,855, filed on Mar. 10, 2003, which claims priority to U.S. Provisional Patent Application Ser. No. 60/395,495, filed on Jul. 12, 2002; and U.S. Provisional Patent Application Ser. No. 60/362,654, filed Mar. 8, 2002. U.S. patent application Ser. No. 10/412,656 also claims priority to U.S. patent application Ser. No. 09/895,857, filed on Jun. 29, 2001, which claims priority to U.S. Patent Application Ser. No. 60/275,621, filed on Mar. 13, 2001. The entire contents of each of the aforementioned applications are incorporated herein by reference.

BACKGROUND OF THE INVENTION

The development of the tetracycline antibiotics was the direct result of a systematic screening of soil specimens collected from many parts of the world for evidence of microorganisms capable of producing bacteriocidal and/or bacteriostatic compositions. The first of these novel compounds was introduced in 1948 under the name chlortetracycline. Two years later, oxytetracycline became available. The elucidation of the chemical structure of these compounds confirmed their similarity and furnished the analytical basis for the production of a third member of this group in 1952, tetracycline. A new family of minocycline compounds, without the ring-attached methyl group present in earlier tetracyclines, was prepared in 1957 and became publicly available in 1967; and minocycline was in use by 1972.

Recently, research efforts have focused on developing new tetracycline antibiotic compositions effective under varying therapeutic conditions and routes of administration. New tetracycline analogues have also been investigated which may prove to be equal to or more effective than the originally introduced minocycline compounds. Examples include U.S. Pat. Nos. 2,980,584; 2,990,331; 3,062,717; 3,165,531; 3,454,697; 3,557,280; 3,674,859; 3,957,980; 4,018,889; 4,024,272; and 4,126,680. These patents are representative of the range of pharmaceutically active tetracycline and tetracycline analogue compositions.

Historically, soon after their initial development and introduction, the tetracyclines were found to be highly effective pharmacologically against rickettsiae; a number of gram-positive and gram-negative bacteria; and the agents responsible for lymphogranuloma venereum, inclusion conjunctivitis, and psittacosis. Hence, tetracyclines became known as "broad spectrum" antibiotics. With the subsequent establishment of their in vitro antimicrobial activity, effectiveness in experimental infections, and pharmacological properties, the tetracyclines as a class rapidly became widely used for therapeutic purposes. However, this widespread use of tetracyclines for both major and minor illnesses and diseases led directly to the emergence of resistance to these antibiotics even among highly susceptible bacterial species both commensal and pathogenic (e.g., *pneumococci* and *Salmonella*). The rise of tetracycline-resistant organisms has resulted in a general decline in use of tetracyclines and tetracycline analogue compositions as antibiotics of choice.

SUMMARY OF THE INVENTION

The invention pertains, at least in part, to compounds of formula I:

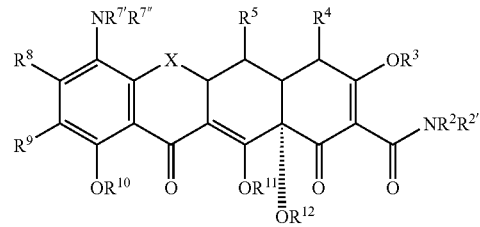

wherein:

X is $CHC(R^{13}Y'Y)$, $CR^{6'}R^{6}$, S, $NR^{6}$, or O;

$R^{2}$, $R^{4'}$, $R^{4''}$, $R^{7'}$ and $R^{7''}$ are each hydrogen, alkyl, alkenyl, alkynyl, alkoxy, alkylthio, alkylsulfinyl, alkylsulfonyl, alkylamino, arylalkyl, aryl, heterocyclic, heteroaromatic or a prodrug moiety;

$R^{4}$ is $NR^{4'}R^{4''}$, alkyl, alkenyl, alkynyl, aryl, hydroxyl, halogen, or hydrogen;

$R^{2'}$, $R^{3}$, $R^{10}$, $R^{11}$ and $R^{12}$ are each hydrogen or a pro-drug moiety;

$R^{5}$ is hydroxyl, hydrogen, thiol, alkanoyl, aroyl, alkaroyl, aryl, heteroaromatic, alkyl, alkenyl, alkynyl, alkoxy, alkylthio, alkylsulfinyl, alkylsulfonyl, alkylamino, arylalkyl, alkyl carbonyloxy, or aryl carbonyloxy;

$R^{6}$ and $R^{6'}$ are independently hydrogen, methylene, absent, hydroxyl, halogen, thiol, alkyl, alkenyl, alkynyl, aryl, alkoxy, alkylthio, alkylsulfinyl, alkylsulfonyl, alkylamino, or an arylalkyl;

$R^{8}$ is hydrogen, hydroxyl, halogen, thiol, alkyl, alkenyl, alkynyl, aryl, alkoxy, alkylthio, alkylsulfinyl, alkylsulfonyl, alkylamino, or an arylalkyl;

$R^{9}$ is aminoalkyl;

$R^{13}$ is hydrogen, hydroxy, alkyl, alkenyl, alkynyl, alkoxy, alkylthio, alkylsulfinyl, alkylsulfonyl, alkylamino, or an arylalkyl;

Y' and Y are each independently hydrogen, halogen, hydroxyl, cyano, sulfhydryl, amino, alkyl, alkenyl, alkynyl, alkoxy, alkylthio, alkylsulfinyl, alkylsulfonyl, alkylamino, or an arylalkyl, and pharmaceutically acceptable salts, esters and prodrugs thereof.

The invention also pertains, at least in part, to compounds of formula (II):

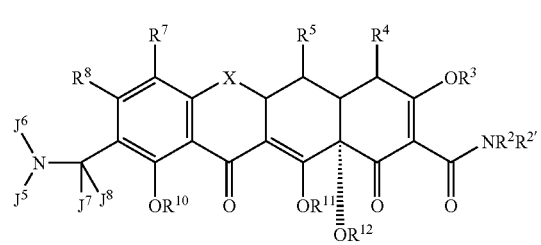

wherein:

$J^{5}$ and $J^{6}$ are each independently hydrogen, alkyl, alkenyl, alkynyl, aryl, sulfonyl, acyl, alkoxycarbonyl, alkaminocarbonyl, alkaminothiocarbonyl, substituted thiocarbonyl, substituted carbonyl, alkoxythiocarbonyl, or linked to form a ring;

$J^{7}$ and $J^{8}$ are each alkyl, halogen, or hydrogen;

X is $CHC(R^{13}Y'Y)$, $CR^{6'}R^{6}$, $C=CR^{6'}R^{6}$, S, $NR^{6}$, or O;

$R^2$, $R^{2'}$, $R^{4'}$, and $R^{4''}$ are each independently hydrogen, alkyl, alkenyl, alkynyl, alkoxy, alkylthio, alkylsulfinyl, alkylsulfonyl, alkylamino, arylalkyl, aryl, heterocyclic, heteroaromatic or a prodrug moiety;

$R^4$ is $NR^{4'}R^{4''}$, alkyl, alkenyl, alkynyl, aryl, hydroxyl, halogen, or hydrogen;

$R^{2'}$, $R^3$, $R^{10}$, $R^{11}$ and $R^{12}$ are each hydrogen or a pro-drug moiety;

$R^5$ is hydroxyl, hydrogen, thiol, alkanoyl, aroyl, alkaroyl, aryl, heteroaromatic, alkyl, alkenyl, alkynyl, alkoxy, alkylthio, alkylsulfinyl, alkylsulfonyl, alkylamino, arylalkyl, alkyl carbonyloxy, or aryl carbonyloxy;

$R^6$ and $R^{6'}$ are each independently hydrogen, methylene, absent, hydroxyl, halogen, thiol, alkyl, alkenyl, alkynyl, aryl, alkoxy, alkylthio, alkylsulfinyl, alkylsulfonyl, alkylamino, or an arylalkyl;

$R^7$ and $R^8$ and are each independently hydrogen, hydroxyl, halogen, thiol, alkyl, alkenyl, alkynyl, aryl, alkoxy, alkylthio, alkylsulfinyl, alkylsulfonyl, alkylamino, or an arylalkyl;

$R^{13}$ is hydrogen, hydroxy, alkyl, alkenyl, alkynyl, alkoxy, alkylthio, alkylsulfinyl, alkylsulfonyl, alkylamino, or an arylalkyl; and Y' and Y are each independently hydrogen, halogen, hydroxyl, cyano, sulfhydryl, amino, alkyl, alkenyl, alkynyl, alkoxy, alkylthio, alkylsulfinyl, alkylsulfonyl, alkylamino, or an arylalkyl, and pharmaceutically acceptable salts thereof A compound of the formula (III):

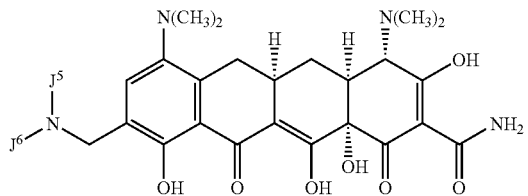

(III)

wherein $J^5$ is alkyl; and $J^6$ is hydrogen, or pharmaceutically acceptable salts, prodrugs and esters thereof.

The invention also pertains to pharmaceutical compositions comprising the compounds of the invention (e.g., compounds of formula (I), (II), (III), or otherwise described herein) and a pharmaceutically acceptable carrier. The invention also pertains to the use of a compound of the invention for the manufacture of a medicament, e.g., a medicament for the treatment of a tetracycline responsive state.

The invention also pertains to methods of using the compounds of the invention to treat subjects suffering from tetracycline compound responsive states.

DETAILED DESCRIPTION OF THE INVENTION

The present invention pertains, at least in part, to novel 9-substituted minocycline compounds. These minocycline compounds can be used to treat numerous tetracycline compound-responsive states, such as bacterial infections and neoplasms, as well as other known applications for minocycline and minocycline compounds in general, such as blocking tetracycline efflux and modulation of gene expression.

The invention pertains, at least in part, to minocycline compounds of Formula I:

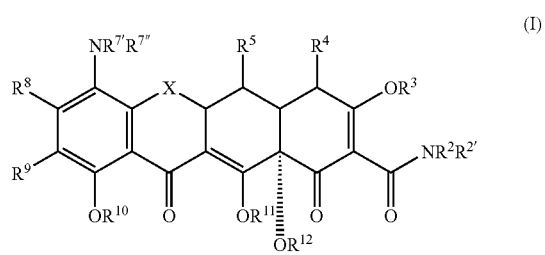

(I)

wherein:

X is $CHC(R^{13}Y'Y)$, $CR^{6'}R^6$, S, $NR^6$, or O;

$R^2$, $R^{4'}$, $R^{4''}$, $R^{7'}$ and $R^{7''}$ are each hydrogen, alkyl, alkenyl, alkynyl, alkoxy, alkylthio, alkylsulfinyl, alkylsulfonyl, alkylamino, arylalkyl, aryl,-heterocyclic, heteroaromatic or a prodrug moiety;

$R^4$ is $NR^{4'}R^{4''}$, alkyl, alkenyl, alkynyl, aryl, hydroxyl, halogen, or hydrogen;

$R^{2'}$, $R^3$, $R^{10}$, $R^{11}$ and $R^{12}$ are each hydrogen or a pro-drug moiety;

$R^5$ is hydroxyl, hydrogen, thiol, alkanoyl, aroyl, alkaroyl, aryl, heteroaromatic, alkyl, alkenyl, alkynyl, alkoxy, alkylthio, alkylsulfinyl, alkylsulfonyl, alkylamino, arylalkyl, alkyl carbonyloxy, or aryl carbonyloxy;

$R^6$ and $R^{6'}$ are independently hydrogen, methylene, absent, hydroxyl, halogen, thiol, alkyl, alkenyl, alkynyl, aryl, alkoxy, alkylthio, alkylsulfinyl, alkylsulfonyl, alkylamino, or an arylalkyl;

$R^8$ is hydrogen, hydroxyl, halogen, thiol, alkyl, alkenyl, alkynyl, aryl, alkoxy, alkylthio, alkylsulfinyl, alkylsulfonyl, alkylamino, or arylalkyl;

$R^9$ is aminoalkyl;

$R^{13}$ is hydrogen, hydroxy, alkyl, alkenyl, alkynyl, alkoxy, alkylthio, alkylsulfinyl, alkylsulfonyl, alkylamino, or an arylalkyl;

Y' and Y are each independently hydrogen, halogen, hydroxyl, cyano, sulfhydryl, amino, alkyl, alkenyl, alkynyl, alkoxy, alkylthio, alkylsulfinyl, alkylsulfonyl, alkylamino, or an arylalkyl, and pharmaceutically acceptable salts, esters and prodrugs thereof.

The term minocycline compounds refers to compounds of formulae (I), (II), and (M) above. In an embodiment, the term minocycline compounds include compounds wherein X is $CR^6R^{6'}$; $R^2$, $R^{2'}$, $R^5$, $R^6$, $R^{6'}$, $R^8$, $R^9$, $R^{10}$, $R^{11}$, and $R^{12}$ are each hydrogen; $R^4$ is $NR^{4'}R^{4''}$; and $R^{4'}$, $R^{4''}$, $R^{7'}$, and $R^{7''}$ are each lower alkyl, e.g., methyl. Other compounds of the invention include compounds wherein $R^4$ is hydrogen.

The invention pertains, at least in part, to compounds of Formula (I) wherein $R^9$ is aminoalkyl (e.g., aminomethyl, e.g., —$CH_2NR'R''$). Aminoalkyl $R^9$ groups may be further substituted. Examples of substituents include alkyl, alkenyl, aryl, alkynyl, carbonyl, and acyl groups. Examples of aryl groups include such as, for example substituted or unsubstituted phenyl (e.g., methylenedioxyphenyl or para-perfluoromethoxyphenyl), or heteroaromatic groups which allows the compound of the invention to perform its intended function. Alkyl groups include methyl, ethyl, i-propyl, n-propyl, i-butyl, n-butyl, t-butyl, pentyl, hexyl, heptyl, octyl, nonyl, decyl, etc. Cyclic alkyl groups include groups with one or more rings, such as, for example, cyclopropane, cyclobutane, cyclopentane, cyclohexane, cycloheptane, etc. In an embodiment, the alkyl $R^9$ group is 2-cyclopentylethyl.

Examples of substituents of alkyl groups include, for example, halogens (e.g. fluorine, chlorine, bromine, iodine, etc.), hydroxyl, alkoxy (e.g., methoxy, ethoxy, propoxy, butoxy, pentoxy, perfluoromethoxy, perchloromethoxy, etc.), alkylcarbonyloxy, arylcarbonyloxy, alkoxycarbonyloxy, aryloxycarbonyloxy, carboxylate, alkylcarbonyl, alkylaminoacarbonyl, arylalkyl aminocarbonyl, alkenylaminocarbonyl, carboxy, alkylcarbonyl, arylcarbonyl, arylalkylcarbonyl, alkenylcarbonyl, alkoxycarbonyl, silyl, aminocarbonyl, alkylthiocarbonyl, phosphate, phosphonato, phosphinato, cyano, amino, acylamino, amido, imino, sulfhydryl, alkylthio, arylthio, thiocarboxylate, sulfate, alkylsulfinyl, alkenyl, sulfonato, sulfamoyl, sulfonamido, nitro, alkenyl, cyano, azido, heterocyclyl, alkylaryl, aryl and heteroaryl.

In a further embodiment, the minocycline compound is selected from the group consisting of:

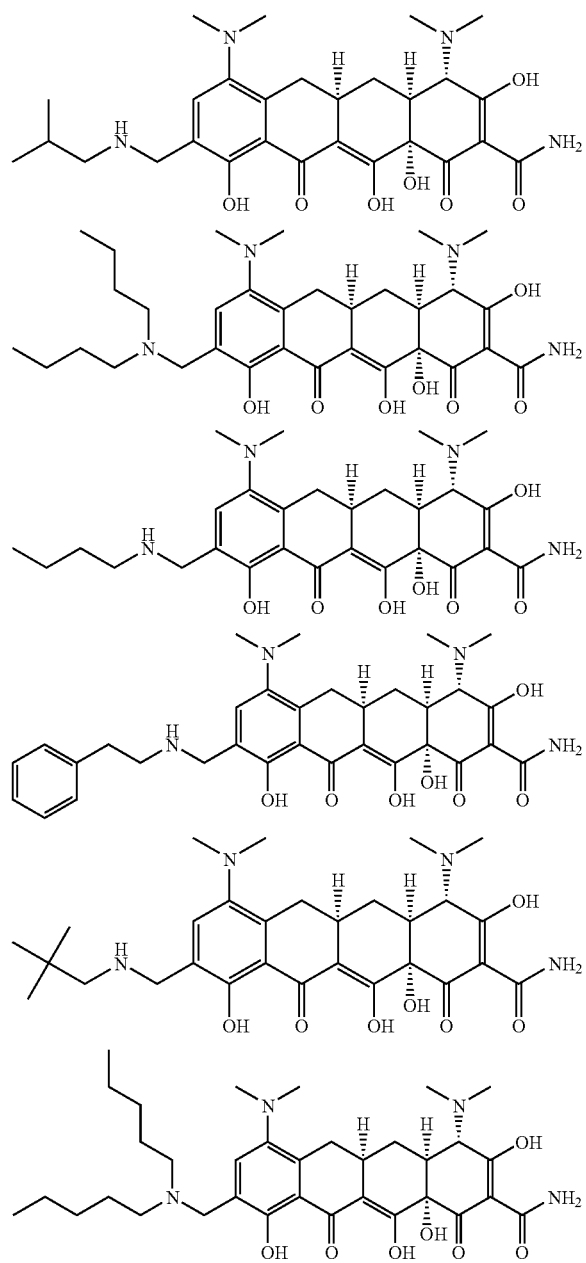

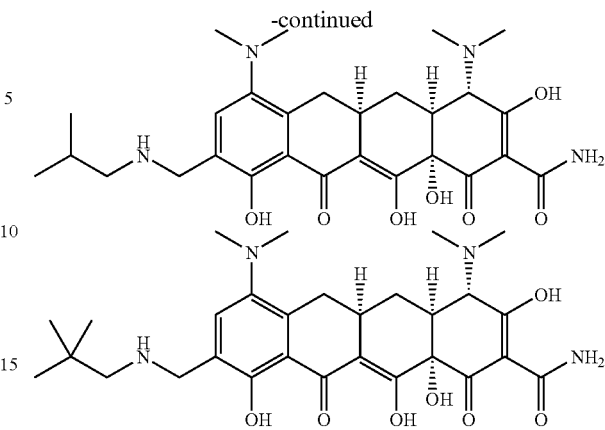

-continued and pharmaceutically acceptable salts, esters and prodrugs thereof.

In another embodiment, the minocycline compound of the invention is a compound wherein $R^9$ is —$CH_2NR^{9c}C(=Z')ZR^{9a}$, wherein Z is $CR^{9d}R^{9e}$, S, $NR^{9b}$ or O; Z' is $NR^{9f}$, O or S; and $R^{9a}$, $R^{9b}$, $R^{9c}$, $R^{9d}$, $R^{9e}$ and $R^{9f}$ are each independently hydrogen, acyl, alkyl, alkenyl, alkynyl, alkoxy, alkylthio, alkylsulfinyl, alkylsulfonyl, alkylamino, arylalkyl, aryl, heterocyclic, heteroaromatic or a prodrug moiety.

In certain embodiments, $R^9$ is —$CH_2NR^{9c}C(=Z')ZR^{9a}$. Examples of $R^{9c}$ include hydrogen. Z' may be, for example, S, NH, or O. Examples of Z include $NR^{9b}$ (e.g., when $R^{9b}$ is hydrogen, alkyl, etc.), O or S.

Examples of $R^{9a}$ groups include aryl groups such as substituted and unsubstituted phenyl. Examples of possible substituents of aryl $R^{9a}$ groups include, but are not limited to, alkyl (e.g., methyl, ethyl, propyl, butyl, pentyl, hexyl, perfluormethyl, perchloroethyl, etc.), alkenyl, halogen (e.g., fluorine, chlorine, bromine, iodine, etc.), hydroxyl, alkoxy (e.g., methoxy, ethoxy, propoxy, perfluoromethoxy, perchloromethoxy, etc.), alkylcarbonyloxy, arylcarbonyloxy, alkoxycarbonyloxy, aryloxycarbonyloxy, carboxylate, alkylcarbonyl, alkylaminoacarbonyl, arylalkyl aminocarbonyl, alkenylaminocarbonyl, alkylcarbonyl, arylcarbonyl, arylalkylcarbonyl, alkenylcarbonyl, alkoxycarbonyl, silyl, aminocarbonyl, alkylthiocarbonyl, phosphate, phosphonato, phosphinato, cyano, amino, acylamino, amido, imino, sulfhydryl, alkylthio, arylthio, thiocarboxylate, sulfate, alkylsulfinyl, sulfonato, sulfamoyl, sulfonamido, nitro, acetyl, alkyl, cyano, azido, heterocyclyl, alkylaryl, aryl and heteroaryl groups.

In certain embodiments, at least one of the substituents of the substituted phenyl is nitro, alkoxy (e.g., methoxy, methylenedioxy, perfluoromethoxy) alkyl (e.g. methyl, ethyl, propyl, butyl, or pentyl), acetyl, halogen (e.g., fluorine, chlorine, bromine, or iodine), or amino (e.g., dialkylamino). In certain embodiments, the alkoxy group is perhalogenated, e.g., perfluoromethoxy.

Examples of aryl $R^{9a}$ groups include, but are not limited to, unsubstituted phenyl, para-nitrophenyl, para-methoxy phenyl, para-perfluoromethoxy phenyl, para-acetyl phenyl, 3,5-methylenedioxyphenyl, 3,5-diperfluoromethyl phenyl, para-bromo phenyl, para-chloro phenyl, and para-fluoro phenyl.

Other examples of aryl $R^{9a}$ groups include substituted and unsubstituted heterocycles (e.g., furanyl, imidazolyl, benzothiophenyl, benzofuranyl, quinolinyl, isoquinolinyl, benzodioxazolyl, benzoxazolyl, benzothiazolyl, benzoimidazolyl, methylenedioxyphenyl, indolyl, thienyl, pyrimidyl, pyrazinyl, purinyl, pyrazolyl, pyrolidinyl, oxazolyl, isooxazolyl, naphthridinyl, thiazolyl, isothiazolyl, or deazapurinyl) and substituted and unsubstituted biaryl groups, such as naphthyl and fluorene.

$R^{9a}$ also may be substituted or unsubstituted alkyl, e.g., methyl, ethyl, propyl, butyl, pentyl, etc. Examples of substituents include but are not limited to halogens (e.g., fluorine, bromine, chlorine, iodine, etc.), hydroxyl, alkoxy (e.g., methoxy, ethoxy, propoxy, butoxy, etc.), alkylcarbonyloxy, arylcarbonyloxy, alkoxycarbonyloxy, aryloxycarbonyloxy, carboxylate, alkylcarbonyl, alkylaminoacarbonyl, arylalkyl aminocarbonyl, alkenylaminocarbonyl, alkylcarbonyl, arylcarbonyl, arylalkylcarbonyl, alkenylcarbonyl, alkoxycarbonyl, silyl, aminocarbonyl, alkylthiocarbonyl, phosphate, phosphonato, phosphinato, cyano, amino, acylamino, amidino, imino, sulfhydryl, alkylthio, arylthio, thiocarboxylate, sulfate, alkylsulfinyl, sulfonato, sulfamoyl, sulfonamido, nitro, trifluoromethyl, cyano, azido, alkenyl, heterocyclyl, alkylaryl, aryl and heteroaryl.

$R^{9a}$ also can be substituted or unsubstituted alkenyl. Examples of substituents for alkenyl $R^{9a}$ groups include those listed above for alkyl $R^{9a}$ groups. Examples of alkenyl $R^{9a}$ groups include pent-1-enyl.

In an embodiment, Z' is NH, Z is NH, and $R^{9a}$ is alkyl.

In a further embodiment, the minocycline compound of the invention does not include compounds wherein $R^9$ is dimethylmaleimido, when $R^9$ is dimethylmaleimido or when the compound is described in Martell et al. (*J. Med. Chem.*, (1967, 10(3), 359-3). In another embodiment, the minocycline compounds of the invention do not include compounds wherein $R^9$ is 4-morpholinylmethyl, when $R^7$ is hydrogen or when the compound is described in Strel'nokov (*Antibiotiki*, (1965), 10(7), 650-6), Polyak (*Ref Zh., Biol. Khim.* Abstr. No. 6F782), Paikin, M. D. (*Ref Zh., Farmakol, Toksikol.* 1965, Abstr. No. 5.54.323), In another embodiment, the compounds of the invention do not include compounds wherein $R^9$ is 1-pyrrolidinylmethyl, when $R^7$ is hydrogen, or compounds otherwise described in Genazzini, E. et al. (*Atti. Soc. Ital. Sci. Vet.* (1964), 18, 175-8, Hajdu, P. *Arzneimittel-Forsch.* (1962), 12, 206-7, *Federal Register*, (1962), 27, 3851, Baldini et al. *Boll. Soc. Ital. Biol. Sper.* (1960), 36, 577-83), Good, W., *Biochim. et Biophys., Acta*, (1962) 56, 359-61; Ritzerfeld, W., *Arzneimittel-Forsch*, (1962), 12, 30-2; Maniar, A. et al., *Ann. Inst. Pasteur*, (1961), 101, 887-97); Garrod, L., *Recenti Progr. Med.* (1962), 32, 3-24; Branceni, *Compt. Rend. Soc. Biol.* (1961), 155, 1469-72, ES 302929, In another embodiment, the compounds of the invention do not include compounds wherein $R^9$ is —CH$_2$NHCH$_2$C(=O)NH$_2$, —CH$_2$NHCH(CH$_3$)C(=O)NH(CH$_2$)$_2$OH, —CH$_2$NHCH(CH$_3$)C(=O)NH$_2$, —CH$_2$NHCH$_2$C(=O)NHCH$_3$, —CH$_2$NHCH$_2$C(=O)NH(CH$_2$)$_2$OH, or —CH$_2$NHCH(C(=O)NH(CH$_2$)$_2$)(CH$_2$)$_4$NH$_2$, or —CH$_2$NHCH(C(=O)(CH$_2$)$_4$NH$_2$, when $R^7$ is H, or otherwise described in GB921252 or GB 955766.

Examples of minocycline compounds of the invention include those listed in Table 1, as well as the ones listed below:

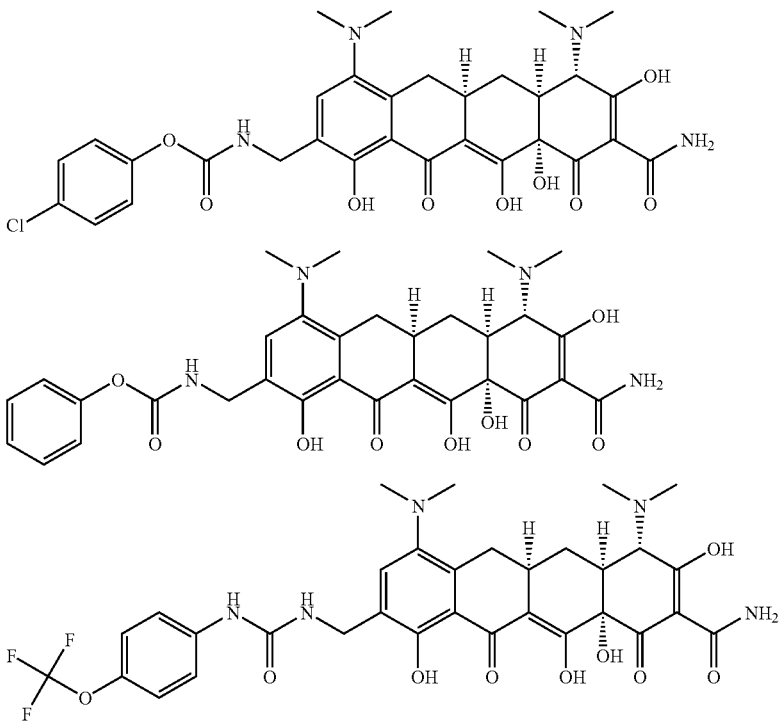

-continued
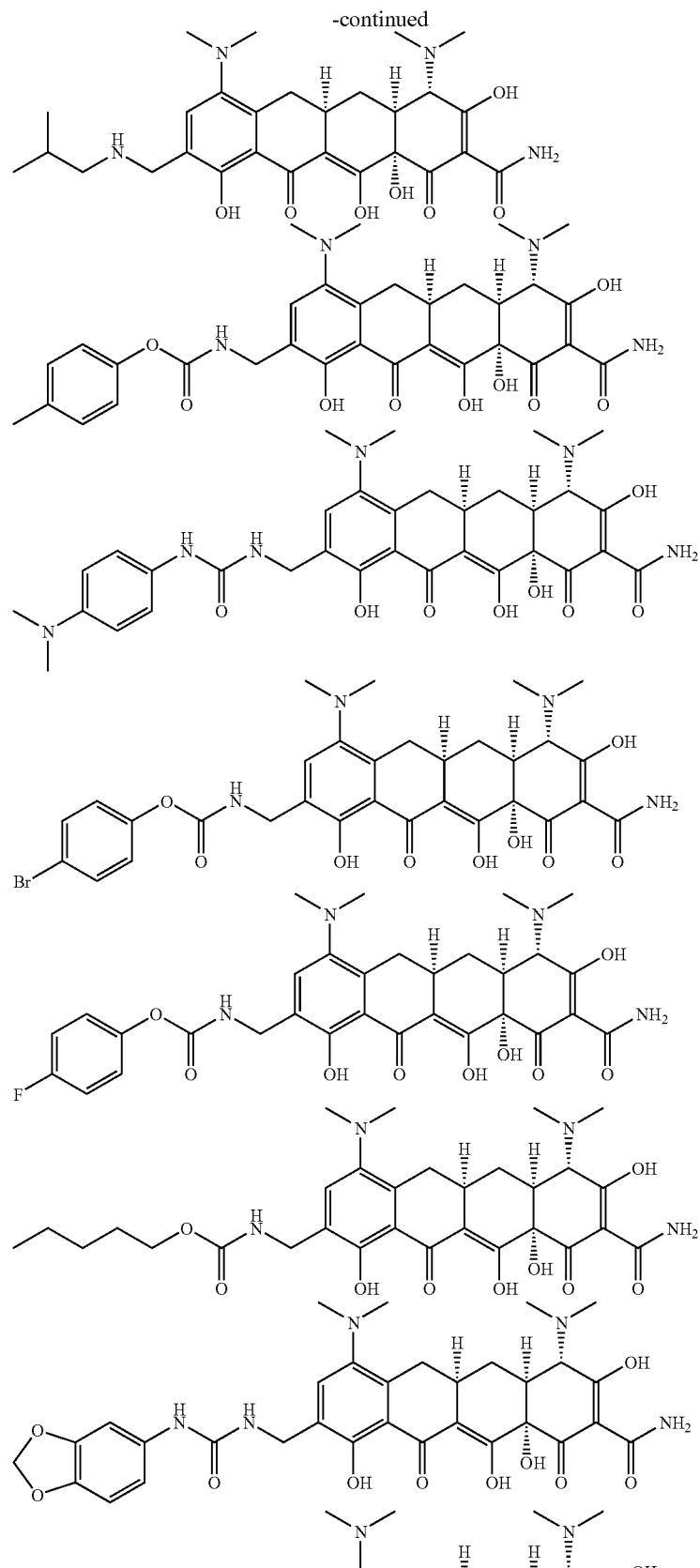

The invention also pertains, at least in part, to minocycline compounds of formula (II):

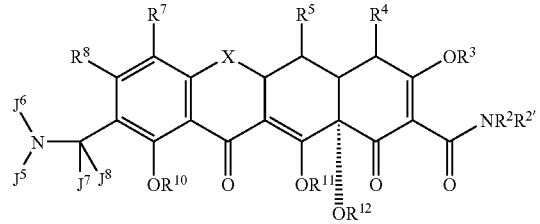

(II)

wherein:

$J^5$ and $J^6$ are each independently hydrogen, alkyl, alkenyl, alkynyl, aryl, sulfonyl, acyl, alkoxycarbonyl, alkaminocarbonyl, alkaminothiocarbonyl, substituted thiocarbonyl, substituted carbonyl, alkoxythiocarbonyl, or linked to form a ring;

$J^7$ and $J^8$ are each alkyl, halogen, or hydrogen;

X is $CHC(R^{13}Y'Y)$, $CR^{6'}R^6$, $C=CR^{6'}R^6$, S, $NR^6$, or O;

$R^2$, $R^{2'}$, $R^{4'}$, and $R^{4''}$ are each independently hydrogen, alkyl, alkenyl, alkynyl, alkoxy, alkylthio, alkylsulfinyl, alkylsulfonyl, alkylamino, arylalkyl, aryl, heterocyclic, heteroaromatic or a prodrug moiety;

$R^4$ is $NR^{4'}R^{4''}$, alkyl, alkenyl, alkynyl, aryl, hydroxyl, halogen, or hydrogen;

$R^{2'}$, $R^3$, $R^{10}$, $R^{11}$ and $R^{12}$ are each hydrogen or a pro-drug moiety;

$R^5$ is hydroxyl, hydrogen, thiol, alkanoyl, aroyl, alkaroyl, aryl, heteroaromatic, alkyl, alkenyl, alkynyl, alkoxy, alkylthio, alkylsulfinyl, alkylsulfonyl, alkylamino, arylalkyl, alkyl carbonyloxy, or aryl carbonyloxy;

$R^6$ and $R^{6'}$ are each independently hydrogen, methylene, absent, hydroxyl, halogen, thiol, alkyl, alkenyl, alkynyl, aryl, alkoxy, alkylthio, alkylsulfinyl, alkylsulfonyl, alkylamino, or an arylalkyl;

$R^8$ and $R^7$ are each independently hydrogen, hydroxyl, halogen, thiol, alkyl, alkenyl, alkynyl, aryl, alkoxy, alkylthio, alkylsulfinyl, alkylsulfonyl, alkylamino, or an arylalkyl;

$R^{13}$ is hydrogen, hydroxy, alkyl, alkenyl, alkynyl, alkoxy, alkylthio, alkylsulfinyl, alkylsulfonyl, alkylamino, or an arylalkyl; and Y' and Y are each independently hydrogen, halogen, hydroxyl, cyano, sulfhydryl, amino, alkyl, alkenyl, alkynyl, alkoxy, alkylthio, alkylsulfinyl, alkylsulfonyl, alkylamino, or an arylalkyl, and pharmaceutically acceptable salts thereof.

In one embodiment, $R^{4'}$ and $R^{4''}$ are each methyl and $R^5$ is hydrogen. In another further embodiment, $J^7$ and $J^8$ are hydrogen. In another embodiment, $J^5$ is substituted or unsubstituted alkyl, e.g., branched or straight chain alkyl. In another embodiment, $J^5$ is methyl, ethyl, propyl, pentyl, hexyl, octyl, etc. In a further embodiment, $J^5$ is n-pentyl. In another further embodiment, $J^6$ is hydrogen.

A compound of the formula (III):

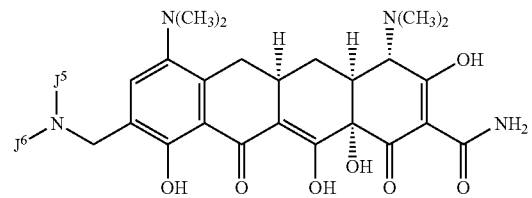

(III)

wherein $J^5$ is alkyl; and $J^6$ is hydrogen, or pharmaceutically acceptable salts, prodrugs and esters thereof.

In a further embodiment, $J^5$ is pentyl, e.g., n-pentyl, and $J^6$ is hydrogen.

The compounds of this invention can be synthesized using the methods described in Schemes 1-7, in combination with methods known in the art. Scheme 1 depicts the reaction of sancycline with an aminoalkylating reagent under appropriate conditions such that an aminoalkyl minocycline compound is formed.

Scheme 1

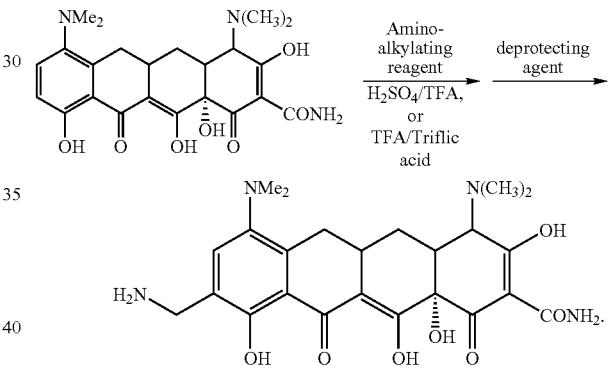

Examples of aminoalkylating reagents, include, but are not limited to, compounds of the formula (IV):

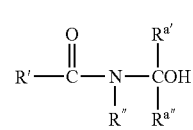

(IV)

wherein $R^{a'}$ and $R^{a''}$ are each independently hydrogen or halogen;

R' is hydrogen, alkyl, alkenyl, alkynyl, aryl, heteroaryl, or halogen; and

R" is hydrogen or optionally linked to R' to form a 4-8 membered ring. The ring may be optionally substituted, e.g., with halogens and may comprise carbons and/or heteroatoms such as oxygen, nitrogen, and sulfur. R' may be further substituted with any substituent which does not prevent the reagent from reacting with the tetracycline compound of the invention, under the appropriate conditions. In another further embodiment, R' is alkyl, e.g., unsubstituted or substituted (e.g., with halogens, e.g., chlorine, fluorine, bromine, iodine, etc.). In another embodiment, R' is aryl, e.g., phenyl, e.g., unsubstituted or substituted (e.g., with halogens (e.g., chlorine, bromine, fluorine, etc.), hydroxy, alkoxy, esters, amino,. etc.). In another embodiment, $R^{a'}$ and $R^{a''}$ are each hydrogen. Other examples of aminoalkylating reagents include N-hydroxymethylphthalimide.

Examples of amino-alkylating reagents include, but are not limited to:

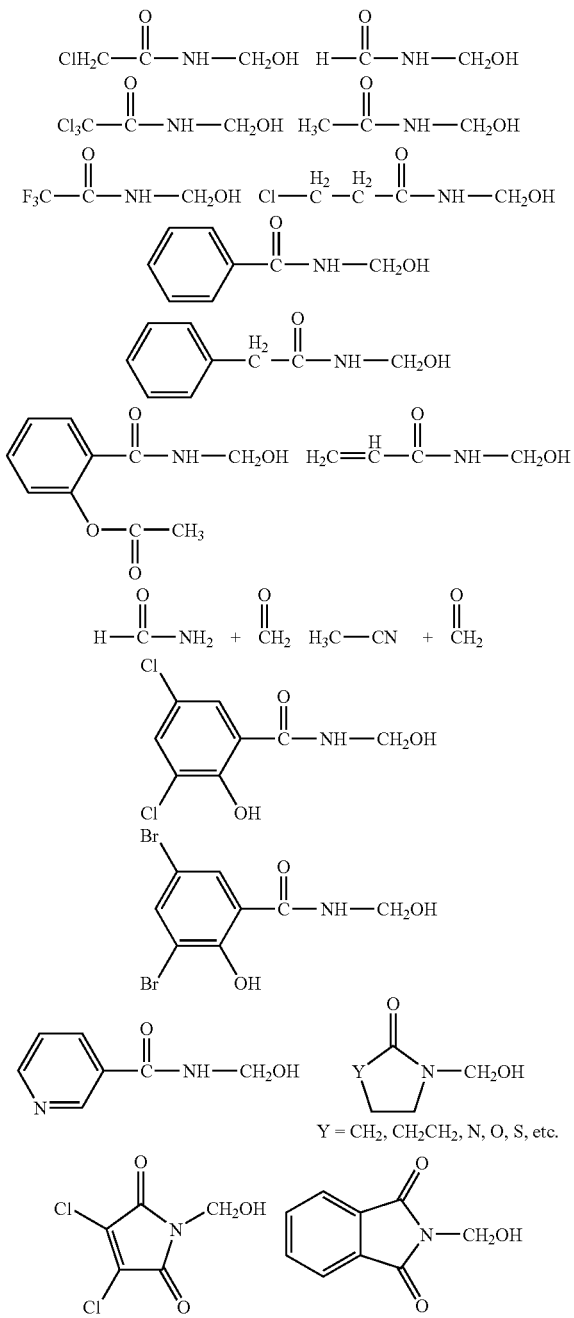

The term "appropriate conditions" include those conditions under which the aminoalkylating reagent and the tetracycline compound interact such that an aminoalkyl tetracycline compound is formed. The appropriate conditions may comprise treating the tetracycline compound with an acid prior to, or concurrently with the addition of the aminoalkylating reagent to the reaction mixture. Examples of acids which maybe used alone or in combination include acids known in the art, as well as, sulfuric acid, hydrofluoric acid (HF), methanesulfonic acid, trifluoromethane sulfonic acid, hydrochloric acid, hydrochloric acid in aqueous ethanol, acetic acid, methanesulfonic acid, and trifluoroacetic acid (TFA). In a further embodiment, appropriate conditions may also comprise treating the resulting tetracycline compound with a reaction quenching agent (e.g., water).

Scheme 2 shows two aminoalkylations of a minocycline compound with aminoalkylating reagents which comprise a 5 membered ring. Similar reactions can be also be carried out using reagents, with, for example, 6- or 7-membered rings.

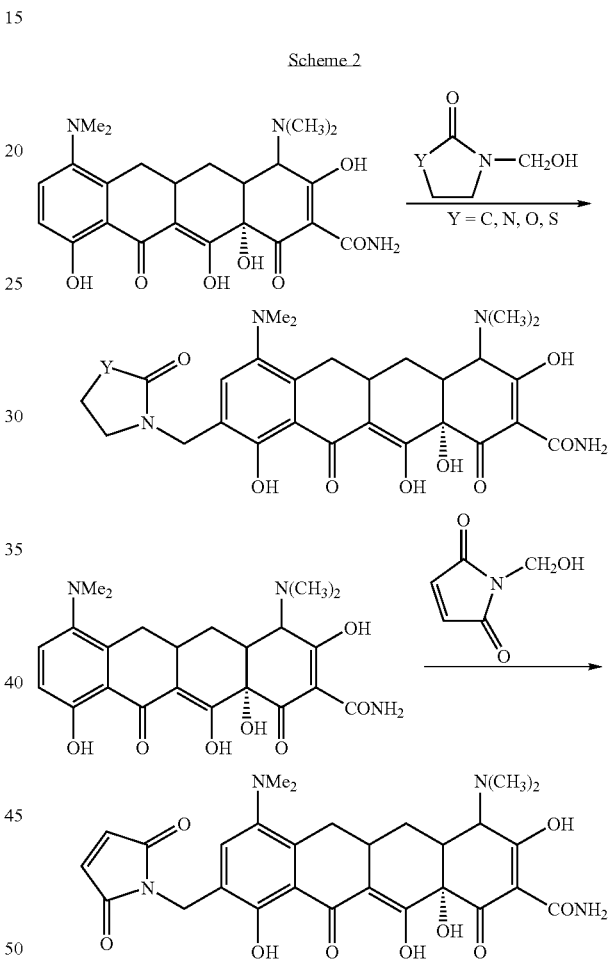

As shown in Scheme 3 below, the synthesis of 7-monosubstituted aminomethyl tetracyclines may be synthesized using protecting groups (i.e. the 9-t-butyl protecting group) to be cleaved using art recognized techniques, such as acid. Examples of acids which can be used include, but are not limited to, HF, trifluoroacetic acid (TFA), $H_2SO_4$ and mixtures thereof. In this way, regioselective aminomethylation at position 7 is achieved.

Scheme 3

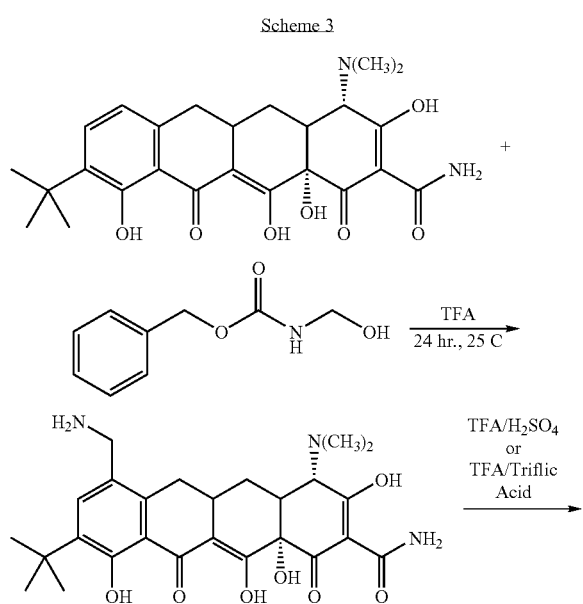

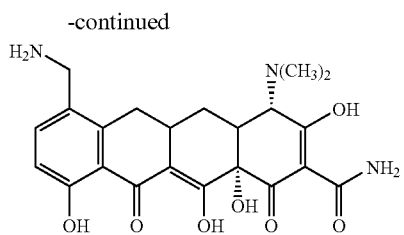

-continued

In a further embodiment, the appropriate conditions may further comprise treating the reaction mixture (which may comprise an intermediate aminoalkyl minocycline compound) with a derivatizing agent under secondary appropriate conditions such that the desired aminoalkyl minocycline compound is formed. The reactions in Scheme 4 are shown for the 9 position, but the reactions are also applicable to other positions of the minocycline compound. Additional derivatizing agents and secondary appropriate conditions may be found, for example, in the chemical literature. See, for example, R. C. LaRock, *Comprehensive Organic Transformations*, (New York: VCH Publishers, Inc., 1989) and references cited therein. Any reagent that can react with a primary amine to form a new compound is possible. Examples of some of the diverse structures are shown in Scheme 4 below.

Scheme 4

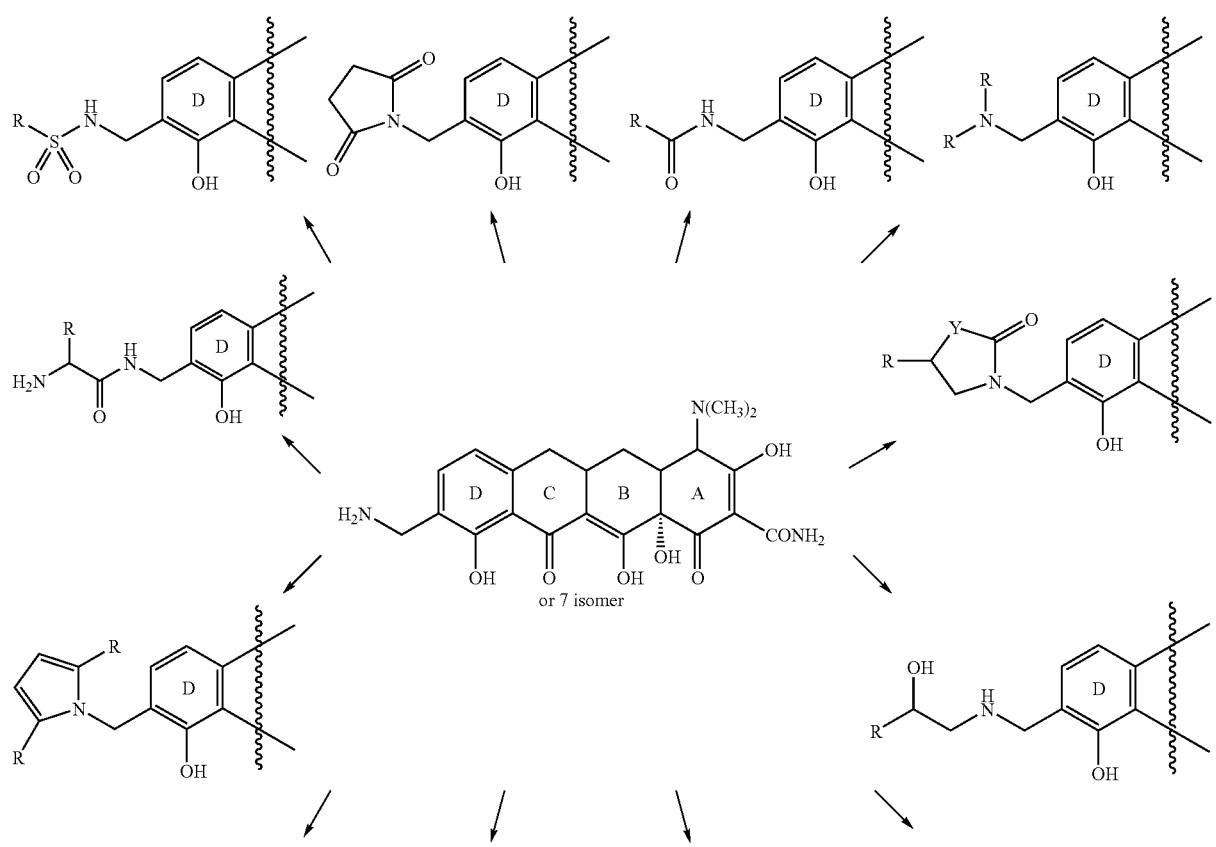

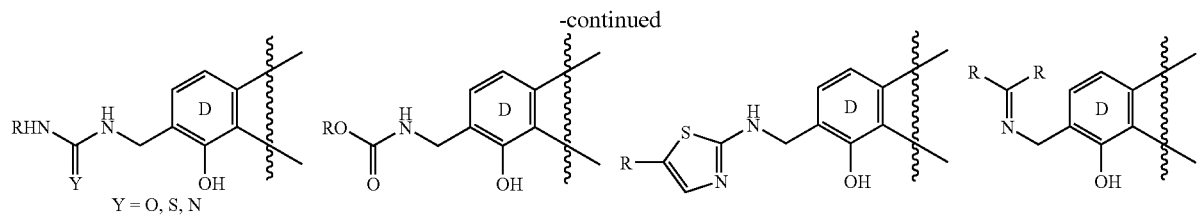

For example, in Scheme 5, an acid chloride derivatizing agent is added to the reaction mixture to form the desired amide aminoalkyl minocycline compound (*J. Am. Chem Soc.* 71, 2215 (1949); *J. Am. Chem. Soc.* 108, 1039 (1986); *Org. Syn. Coll. Vol.* 4, 339 (1963); *Org. Syn. Coll. Vol.* 5, 387 (1973)).

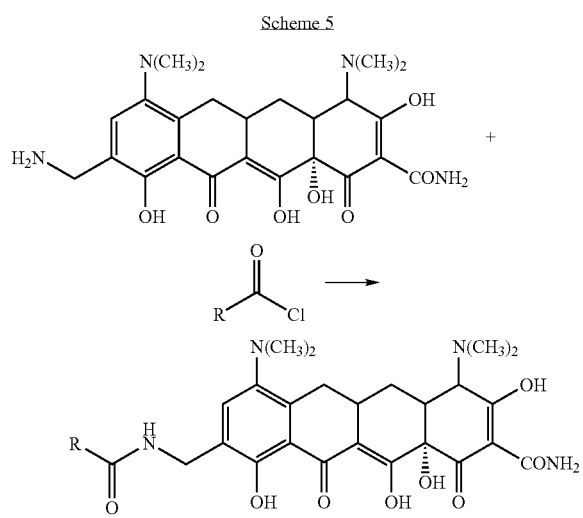

Scheme 6 depicts the reaction of an intermediate aminoalkyl minocycline compound with an appropriate sulfonyl chloride derivatizing agent, such that the desired sulfonamide aminoalkyl compound is formed (*Org. Syn. Coll. Vol.* 5, 736, 758 (1973)).

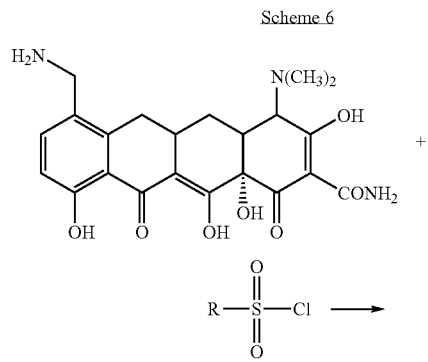

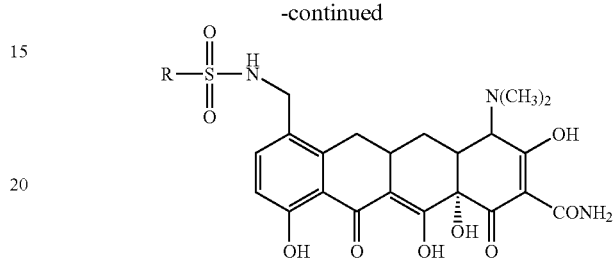

Scheme 7 depicts the reaction of a derivatizing agent with an aminoalkyl tetracycline intermediate to form the resulting carbamate aminoalkyl minocycline compound.

The term "alkyl" includes saturated aliphatic groups, including straight-chain alkyl groups (e.g., methyl, ethyl, propyl, butyl, pentyl, hexyl, heptyl, octyl, nonyl, decyl, etc.), branched-chain alkyl groups (isopropyl, tert-butyl, isobutyl, etc.), cycloalkyl (alicyclic) groups (cyclopropyl, cyclopentyl, cyclohexyl, cycloheptyl, cyclooctyl), alkyl substituted cycloalkyl groups, and cycloalkyl substituted alkyl groups. The term alkyl further includes alkyl groups, which can further include oxygen, nitrogen, sulfur or phosphorous atoms replacing one or more carbons of the hydrocarbon backbone. In certain embodiments, a straight chain or branched chain alkyl has 6 or fewer carbon atoms in its backbone (e.g., $C_1$-$C_6$ for straight chain, $C_3$-$C_6$ for branched chain), and more preferably 4 or fewer. Likewise, preferred cycloalkyls have from 3-8 carbon atoms in their ring structure, and more preferably have 5 or 6 carbons in the ring structure. The term $C_1$-$C_6$ includes alkyl groups containing 1 to 6 carbon atoms.

Moreover, the term alkyl includes both "unsubstituted alkyls" and "substituted alkyls", the latter of which refers to alkyl moieties having substituents replacing a hydrogen on one or more carbons of the hydrocarbon backbone. Such substituents can include, for example, alkenyl, alkynyl, halogen, hydroxyl, alkylcarbonyloxy, arylcarbonyloxy, alkoxycarbonyloxy, aryloxycarbonyloxy, carboxylate, alkylcarbonyl, arylcarbonyl, alkoxycarbonyl, aminocarbonyl, alkylaminocarbonyl, dialkylaminocarbonyl, alkylthiocarbonyl, alkoxyl, phosphate, phosphonato, phosphinato, cyano, amino (including alkyl amino, dialkylamino, arylamino, diarylamino, and alkylarylamino), acylamino (including alkylcarbonylamino, arylcarbonylamino, carbamoyl and ureido), amidino, imino, sulfhydryl, alkylthio, arylthio, thiocarboxylate, sulfates, alkylsulfinyl, sulfonato, sulfamoyl, sulfonamido, nitro, trifluoromethyl, cyano, azido, heterocyclyl, alkylaryl, or an aromatic or heteroaromatic moiety. Cycloalkyls can be further substituted, e.g., with the substituents described above. An "alkylaryl" or an "arylalkyl" moiety is an alkyl substituted with an aryl (e.g., phenylmethyl (benzyl)). The term "alkyl" also includes the side chains of natural and unnatural amino acids.

The term "aryl" includes groups, including 5- and 6-membered single-ring aromatic groups that may include from zero to four heteroatoms, for example, benzene, phenyl, pyrrole, furan, thiophene, thiazole, isothiaozole, imidazole, triazole, tetrazole, pyrazole, oxazole, isooxazole, pyridine, pyrazin, pyridazine, and pyrimidine, and the like. Furthermore, the term "aryl" includes multicyclic aryl groups, e.g., tricyclic, bicyclic, e.g., naphthalene, benzoxazole, benzodioxazole, benzothiazole, benzoimidazole, benzothiophene, methylenedioxyphenyl, quinoline, isoquinoline, napthridine, indole, benzofuran, purine, benzofuran, deazapurine, or indolizine. Those aryl groups having heteroatoms in the ring structure may also be referred to as "aryl heterocycles", "heterocycles," "heteroaryls" or "heteroaromatics". The aromatic ring can be substituted at one or more ring positions with such substituents as described above, as for example, halogen, hydroxyl, alkoxy, alkylcarbonyloxy, arylcarbonyloxy, alkoxycarbonyloxy, aryloxycarbonyloxy, carboxylate, alkylcarbonyl, alkylaminoacarbonyl, arylalkyl aminoacarbonyl, alkenylaminocarbonyl, alkylcarbonyl, arylcarbonyl, arylalkylcarbonyl, alkenylcarbonyl, alkoxycarbonyl, aminocarbonyl, alkylthiocarbonyl, phosphate, phosphonato, phosphinato, cyano, amino (including alkyl amino, dialkylamino, arylamino, diarylamino, and alkylarylamino), acylamino (including alkylcarbonylamino, arylcarbonylamino, carbamoyl and ureido), amidino, imino, sulfhydryl, alkylthio, arylthio, thiocarboxylate, sulfates, alkylsulfinyl, sulfonato, sulfamoyl, sulfonamido, nitro, trifluoromethyl, cyano, azido, heterocyclyl, alkylaryl, or an aromatic or heteroaromatic moiety. Aryl groups can also be fused or bridged with alicyclic or heterocyclic rings which are not aromatic so as to form a polycycle (e.g., tetralin).

The term "alkenyl" includes unsaturated aliphatic groups analogous in length and possible substitution to the alkyls described above, but that contain at least one double bond.

For example, the term "alkenyl" includes straight-chain alkenyl groups (e.g., ethylenyl, propenyl, butenyl, pentenyl, hexenyl, heptenyl, octenyl, nonenyl, decenyl, etc.), branched-chain alkenyl groups, cycloalkenyl (alicyclic) groups (cyclopropenyl, cyclopentenyl, cyclohexenyl, cycloheptenyl, cyclooctenyl), alkyl or alkenyl substituted cycloalkenyl groups, and cycloalkyl or cycloalkenyl substituted alkenyl groups. The term alkenyl further includes alkenyl groups which include oxygen, nitrogen, sulfur or phosphorous atoms replacing one or more carbons of the hydrocarbon backbone. In certain embodiments, a straight chain or branched chain alkenyl group has 6 or fewer carbon atoms in its backbone (e.g., $C_2$-$C_6$ for straight chain, $C_3$-$C_6$ for branched chain). Likewise, cycloalkenyl groups may have from 3-8 carbon atoms in their ring structure, and more preferably have 5 or 6 carbons in the ring structure. The term $C_2$-$C_6$ includes alkenyl groups containing 2 to 6 carbon atoms.

Moreover, the term alkenyl includes both "unsubstituted alkenyls" and "substituted alkenyls", the latter of which refers to alkenyl moieties having substituents replacing a hydrogen on one or more carbons of the hydrocarbon backbone. Such substituents can include, for example, alkyl groups, alkynyl groups, halogens, hydroxyl, alkylcarbonyloxy, arylcarbonyloxy, alkoxycarbonyloxy, aryloxycarbonyloxy, carboxylate, alkylcarbonyl, arylcarbonyl, alkoxycarbonyl, aminocarbonyl, alkylaminocarbonyl, dialkylaminocarbonyl, alkylthiocarbonyl, alkoxyl, phosphate, phosphonato, phosphinato, cyano, amino (including alkyl amino, dialkylamino, arylamino, diarylamino, and alkylarylamino), acylamino (including alkylcarbonylamino, arylcarbonylamino, carbamoyl and ureido), amidino, imino, sulfhydryl, alkylthio, arylthio, thiocarboxylate, sulfates, alkylsulfinyl, sulfonato, sulfamoyl, sulfonamido, nitro, trifluoromethyl, cyano, azido, heterocyclyl, alkylaryl, or an aromatic or heteroaromatic moiety.

The term "alkynyl" includes unsaturated aliphatic groups analogous in length and possible substitution to the alkyls described above, but. which contain at least one triple bond.

For example, the term "alkynyl" includes straight-chain alkynyl groups (e.g., ethynyl, propynyl, butynyl, pentynyl, hexynyl, heptynyl, octynyl, nonynyl, decynyl, etc.), branched-chain alkynyl groups, and cycloalkyl or cycloalkenyl substituted alkynyl groups. The term alkynyl further includes alkynyl groups which include oxygen, nitrogen, sulfur or phosphorous atoms replacing one or more carbons of the hydrocarbon backbone. In certain embodiments, a straight chain or branched chain alkynyl group has 6 or fewer carbon atoms in its backbone (e.g., $C_2$-$C_6$ for straight chain, $C_3$-$C_6$ for branched chain). The term $C_2$-$C_6$ includes alkynyl groups containing 2 to 6 carbon atoms.

Moreover, the term alkynyl includes both "unsubstituted alkynyls" and "substituted alkynyls", the latter of which refers to alkynyl moieties having substituents replacing a hydrogen on one or more carbons of the hydrocarbon backbone. Such substituents can include, for example, alkyl groups, alkynyl groups, halogens, hydroxyl, alkylcarbonyloxy, arylcarbonyloxy, alkoxycarbonyloxy, aryloxycarbonyloxy, carboxylate, alkylcarbonyl, arylcarbonyl, alkoxycarbonyl, aminocarbonyl, alkylaminocarbonyl, dialkylaminocarbonyl, alkylthiocarbonyl, alkoxyl, phosphate, phosphonato, phosphinato, cyano, amino (including alkyl amino, dialkylamino, arylamino, diarylamino, and alkylarylamino), acylamino (including alkylcarbonylamino, arylcarbonylamino, carbamoyl and ureido), amidino, imino, sulfhydryl, alkylthio, arylthio, thiocarboxylate, sulfates, alkylsulfinyl, sulfonato, sulfamoyl, sulfonamido, nitro, trifluoromethyl, cyano, azido, heterocyclyl, alkylaryl, or an aromatic or heteroaromatic moiety.

Unless the number of carbons is otherwise specified, "lower alkyl" as used herein means an alkyl group, as defined above, but having from one to five carbon atoms in its backbone structure. "Lower alkenyl" and "lower alkynyl" have chain lengths of, for example, 2-5 carbon atoms.

The term "acyl" includes compounds and moieties which contain the acyl radical ($CH_3CO$—) or a carbonyl group. The term "substituted acyl" includes acyl groups where one or more of the hydrogen atoms are replaced by for example, alkyl groups, alkynyl groups, halogens, hydroxyl, alkylcarbonyloxy, arylcarbonyloxy, alkoxycarbonyloxy, aryloxycarbonyloxy, carboxylate, alkylcarbonyl, arylcarbonyl, alkoxycarbonyl, aminocarbonyl, alkylaminocarbonyl, dialkylaminocarbonyl, alkylthiocarbonyl, alkoxyl, phosphate, phosphonato, phosphinato, cyano, amino (including alkyl amino, dialkylamino, arylamino, diarylamino, and alkylarylamino), acylamino (including alkylcarbonylamino, arylcarbonylamino, carbamoyl and ureido), amidino, imino, sulfhydryl, alkylthio, arylthio, thiocarboxylate, sulfates, alkylsulfinyl, sulfonato, sulfamoyl, sulfonamido, nitro, trifluoromethyl, cyano, azido, heterocyclyl, alkylaryl, or an aromatic or heteroaromatic moiety.

The term "acylamino" includes moieties wherein an acyl moiety is bonded to an amino group. For example, the term includes alkylcarbonylamino, arylcarbonylamino, carbamoyl and ureido groups.

The term "aroyl" includes compounds and moieties with an aryl or heteroaromatic moiety bound to a carbonyl group. Examples of aroyl groups include phenylcarboxy, naphthyl carboxy, etc.

The terms "alkoxyalkyl", "alkylaminoalkyl" and "thioalkoxyalkyl" include alkyl groups, as described above, which further include oxygen, nitrogen or sulfur atoms replacing one or more carbons of the hydrocarbon backbone, e.g., oxygen, nitrogen or sulfur atoms.

The term "alkoxy" includes substituted and unsubstituted alkyl, alkenyl, and alkynyl groups covalently linked to an oxygen atom. Examples of alkoxy groups include methoxy, ethoxy, isopropyloxy, propoxy, butoxy, and pentoxy groups. Examples of substituted alkoxy groups include halogenated alkoxy groups. The alkoxy groups can be substituted with groups such as alkenyl, alkynyl, halogen, hydroxyl, alkylcarbonyloxy, arylcarbonyloxy, alkoxycarbonyloxy, aryloxycarbonyloxy, carboxylate, alkylcarbonyl, arylcarbonyl, alkoxycarbonyl, aminocarbonyl, alkylaminocarbonyl, dialkylaminocarbonyl, alkylthiocarbonyl, alkoxyl, phosphate, phosphonato, phosphinato, cyano, amino (including alkyl amino, dialkylamino, arylamino, diarylamino, and alkylarylamino), acylamino (including alkylcarbonylamino, arylcarbonylamino, carbamoyl and ureido), amidino, imino, sulfhydryl, alkylthio, arylthio, thiocarboxylate, sulfates, alkylsulfinyl, sulfonato, sulfamoyl, sulfonamido, nitro, trifluoromethyl, cyano, azido, heterocyclyl, alkylaryl, or an aromatic or heteroaromatic moieties. Examples of halogen substituted alkoxy groups include, but are not limited to, fluoromethoxy, difluoromethoxy, trifluoromethoxy, chloromethoxy, dichloromethoxy, trichloromethoxy, etc.

The term "amine" or "amino" includes compounds where a nitrogen atom is covalently bonded to at least one carbon or heteroatom. The term "alkyl amino" includes groups and compounds wherein the nitrogen is bound to at least one additional alkyl group. The term "dialkyl amino" includes groups wherein the nitrogen atom is bound to at least two additional alkyl groups. The term "arylamino" and "diarylamino" include groups wherein the nitrogen is bound to at least one or two aryl groups, respectively. The term "alkylarylamino," "alkylaminoaryl" or "arylaminoalkyl" refers to an amino group which is bound to at least one alkyl group and at least one aryl group. The term "alkaminoalkyl" refers to an alkyl, alkenyl, or alkynyl group bound to a nitrogen atom which is also bound to an alkyl group.

The term "amide" or "aminocarbonyl" includes compounds or moieties which contain a nitrogen atom which is bound to the carbon of a carbonyl or a thiocarbonyl group. The term includes "alkaminocarbonyl" or "alkylaminocarbonyl" groups which include alkyl, alkenyl, aryl or alkynyl groups bound to an amino group bound to a carbonyl group. It includes arylaminocarbonyl groups which include aryl or heteroaryl moieties bound to an amino group which is bound to the carbon of a carbonyl or thiocarbonyl group. The terms "alkylaminocarbonyl," "alkenylaminocarbonyl," "alkynylaminocarbonyl," "arylaminocarbonyl," "alkylcarbonylamino," "alkenylcarbonylamino," "alkynylcarbonylamino," and "arylcarbonylamino" are included in term "amide." Amides also include urea groups (aminocarbonylamino) and carbamates (oxycarbonylamino).

The term "carbonyl" or "carboxy" includes compounds and moieties which contain a carbon connected with a double bond to an oxygen atom. Examples of moieties which contain a carbonyl include aldehydes, ketones, carboxylic acids, amides, esters, anhydrides, etc.

The term "thiocarbonyl" or "thiocarboxy" includes compounds and moieties which contain a carbon connected with a double bond to a sulfur atom.

The term "ether" includes compounds or moieties which contain an oxygen bonded to different carbon atoms or heteroatoms. For example, the term includes "alkoxyalkyl" which refers to an alkyl, alkenyl, or alkynyl group covalently bonded to an oxygen atom which is covalently bonded to another alkyl group.

The term "ester" includes compounds and moieties which contain a carbon or a heteroatom bound to an oxygen atom which is bonded to the carbon of a carbonyl group. The term "ester" includes alkoxycarboxy groups such as methoxycarbonyl, ethoxycarbonyl, propoxycarbonyl, butoxycarbonyl, pentoxycarbonyl, etc. The alkyl, alkenyl, or alkynyl groups are as defined above.

The term "thioether" includes compounds and moieties which contain a sulfur atom bonded to two different carbon or hetero atoms. Examples of thioethers include, but are not limited to alkthioalkyls, alkthioalkenyls, and alkthioalkynyls. The term "alkthioalkyls" include compounds with an alkyl, alkenyl, or alkynyl group bonded to a sulfur atom which is bonded to an alkyl group. Similarly, the term "alkthioalkenyls" and alkthioalkynyls" refer to compounds or moieties wherein an alkyl, alkenyl, or alkynyl group is bonded to a sulfur atom which is covalently bonded to an alkynyl group.

The term "hydroxy" or "hydroxyl" includes groups with an —OH or —O$^-$.

The term "halogen" includes fluorine, bromine, chlorine, iodine, etc. The term "perhalogenated" generally refers to a moiety wherein all hydrogens are replaced by halogen atoms.

The terms "polycyclyl" or "polycyclic radical" refer to two or more cyclic rings (e.g., cycloalkyls, cycloalkenyls, cycloalkynyls, aryls and/or heterocyclyls) in which two or more carbons are common to two adjoining rings, e.g., the rings are "fused rings". Rings that are joined through non-adjacent atoms are termed "bridged" rings. Each of the rings of the polycycle can be substituted with such substituents as described above, as for example, halogen, hydroxyl, alkylcarbonyloxy, arylcarbonyloxy, alkoxycarbonyloxy, aryloxycarbonyloxy, carboxylate, alkylcarbonyl, alkoxycarbonyl, alkylaminoacarbonyl, arylalkylaminocarbonyl, alkenylaminocarbonyl, alkylcarbonyl, arylcarbonyl, arylalkyl carbonyl, alkenylcarbonyl, aminocarbonyl, alkylthiocarbonyl, alkoxyl, phosphate, phosphonato, phosphinato, cyano, amino (including alkyl amino, dialkylamino, arylamino, diarylamino, and alkylarylamino), acylamino (including alkylcarbonylamino, arylcarbonylamino, carbamoyl and ureido), amidino, imino, sulfhydryl, alkylthio, arylthio, thiocarboxylate, sulfates, alkylsulfinyl, sulfonato, sulfamoyl, sulfonamido, nitro, trifluoromethyl, cyano, azido, heterocyclyl, alkyl, alkylaryl, or an aromatic or heteroaromatic moiety.

The term "heteroatom" includes atoms of any element other than carbon or hydrogen. Preferred heteroatoms are nitrogen, oxygen, sulfur and phosphorus.

The term "prodrug moiety" includes moieties which can be metabolized in vivo to an active group and moieties which may advantageously remain attached in vivo. Preferably, the prodrugs moieties are metabolized in vivo by enzymes, e.g., esterases or by other mechanisms to hydroxyl groups or other advantageous groups. Examples of prodrugs and their uses are well known in the art (See, e.g., Berge et al. (1977) "Pharmaceutical Salts", *J. Pharm. Sci.* 66:1-19). The prodrugs can be prepared in situ during the final isolation and purification of the compounds, or by separately reacting the purified compound with a suitable agent. Hydroxyl groups can be converted into esters via treatment with a carboxylic acid. Examples of prodrug moieties include substituted and unsubstituted, branch or unbranched lower alkyl ester moieties, (e.g., propionoic acid esters), lower alkenyl esters, di-lower alkyl-amino lower-alkyl esters (e.g., dimethylaminoethyl ester), acylamino lower alkyl esters (e.g., acetyloxymethyl ester), acyloxy lower alkyl esters (e.g., pivaloyloxymethyl ester), aryl esters (phenyl ester), aryl-lower alkyl esters (e.g., benzyl ester), substituted (e.g., with methyl, halo, or methoxy substituents) aryl and aryl-lower alkyl esters, amides, lower-alkyl amides, di-lower alkyl amides, and hydroxy amides. Preferred prodrug moieties are propionoic acid esters and acyl esters.

It will be noted that the structure of some of the compounds of this invention includes asymmetric carbon atoms. It is to be understood accordingly that the isomers arising from such asymmetry (e.g., all enantiomers and diastereomers) are included within the scope of this invention, unless indicated otherwise. Such isomers can be obtained in substantially pure form by classical separation techniques and by stereochemically controlled synthesis. Furthermore, the structures and other compounds and moieties discussed in this application also include all tautomers thereof.

The invention also pertains to methods for treating a tetracycline responsive states in subjects, by administering to a subject an effective amount of a compound of the invention (e.g., a compound of Formula (I), (II), (III), or otherwise described herein), such that the tetracycline responsive state is treated.

The language "tetracycline compound responsive state" or "tetracycline responsive state" includes states which can be treated, prevented, or otherwise ameliorated by the administration of a compound of the invention, e.g., a compound of Formula (I), (II), (III) or otherwise described herein. Tetracycline compound responsive states include bacterial, viral, and fugal infections (including those which are resistant to other tetracycline compounds), cancer (e.g., prostate, breast, colon, lung melanoma and lymph cancers and other disorders characterized by unwanted cellular proliferation, including, but not limited to, those described in U.S. Pat. No. 6,100,248), arthritis, osteoporosis, diabetes, cystic fibrosis, neurological disorders and other states for which tetracycline compounds have been found to be active (see, for example, U.S. Pat. Nos. 5,789,395; 5,834,450; 6,277,061 and 5,532,227, each of which is expressly incorporated herein by reference). Compounds of the invention can be used to prevent or control important mammalian and veterinary diseases such as diarrhea, urinary tract infections, infections of skin and skin structure, ear, nose and throat infections, wound infection, mastitis and the like. In addition, methods for treating neoplasms using tetracycline compounds of the invention are also included (van der Bozert et al., *Cancer Res.*, 48:6686-6690 (1988)). In a further embodiment, the tetracycline responsive state is not a bacterial infection. Other tetracycline compound responsive states include, for example, those described in U.S. Ser. No. 10/196,010.

Tetracycline compound responsive states also include inflammatory process associated states (IPAS). The term "inflammatory process associated state" includes states in which inflammation or inflammatory factors (e.g., matrix metalloproteinases (MMPs), nitric oxide (NO), TNF, interleukins, plasma proteins, cellular defense systems, cytokines, lipid metabolites, proteases, toxic radicals, adhesion molecules, etc.) are involved or are present in an area in aberrant amounts, e.g., in amounts which may be advantageous to alter, e.g., to benefit the subject. The inflammatory process is the response of living tissue to damage. The cause of inflammation may be due to physical damage, chemical substances, micro-organisms, tissue necrosis, cancer or other agents. Acute inflammation is short-lasting, lasting only a few days. If it is longer lasting however, then it may be referred to as chronic inflammation.

IPAS's include inflammatory disorders. Inflammatory disorders are generally characterized by heat, redness, swelling, pain and loss of function. Examples of causes of inflammatory disorders include, but are not limited to, microbial infections (e.g., bacterial and fungal infections), physical agents (e.g., burns, radiation, and trauma), chemical agents (e.g., toxins and caustic substances), tissue necrosis and various types of immunologic reactions.

Examples of inflammatory disorders include, but are not limited to, osteoarthritis, rheumatoid arthritis, acute and chronic infections (bacterial and fungal, including diphtheria and pertussis); acute and chronic bronchitis, sinusitis, and upper respiratory infections, including the common cold; acute and chronic gastroenteritis and colitis; acute and chronic cystitis and urethritis; acute and chronic dermatitis; acute and chronic conjunctivitis; acute and chronic serositis (pericarditis, peritonitis, synovitis, pleuritis and tendinitis); uremic pericarditis; acute and chronic cholecystis; acute and chronic vaginitis; acute and chronic uveitis; drug reactions; insect bites; burns (thermal, chemical, and electrical); and sunburn.

Tetracycline compound responsive states also include NO associated states. The term "NO associated state" includes states which involve or are associated with nitric oxide (NO) or inducible nitric oxide synthase (iNOS). NO associated state includes states which are characterized by aberrant amounts of NO and/or iNOS. Preferably, the NO associated state can be treated by administering tetracycline compounds of the invention, e.g., compounds of formula I, II, III, or otherwise described herein. The disorders, diseases and states described in U.S. Pat. Nos. 6,231,894; 6,015,804; 5,919,774; and 5,789,395 are also included as NO associated states. The entire contents of each of these patents are hereby incorporated herein by reference.

Other examples of NO associated states include, but are not limited to, malaria, senescence, diabetes, vascular stroke, neurodegenerative disorders (Alzheimer's disease, Huntington's disease), cardiac disease ( reperfusion-associated injury following infarction), juvenile diabetes, inflammatory disorders, osteoarthritis, rheumatoid arthritis, acute and chronic infections (bacterial, viral, and fungal); cystic fibrosis, acute and chronic bronchitis, sinusitis, and respiratory infections, including the common cold; acute and chronic gastroenteritis and colitis; acute and chronic cystitis and urethritis; acute and chronic dermatitis; acute and chronic conjunctivitis; acute and chronic serositis (pericarditis, peritonitis, synovitis, pleuritis and tendinitis); uremic pericarditis; acute and chronic cholecystis; acute and chronic vaginitis; acute and chronic uveitis; drug reactions; insect bites; burns (thermal, chemical, and electrical); and sunburn.

The term "inflammatory process associated state" also includes, in one embodiment, matrix metalloproteinase associated states (MMPAS). MMPAS include states characterized by aberrant amounts of MMPs or MMP activity. These are also include as tetracycline compound responsive states which may be treated using compounds of the invention, e.g., in formula (I), (II), (III) or otherwise described herein.

Examples of matrix metalloproteinase associated states ("MMPAS's") include, but are not limited to, arteriosclerosis, corneal ulceration, emphysema, osteoarthritis, multiple sclerosis (Liedtke et al., *Ann. Neurol.* 1998, 44:35-46; Chandler et al, *J. Neuroimmunol.* 1997, 72:155-71), osteosarcoma, osteomyelitis, bronchiectasis, chronic pulmonary obstructive disease, skin and eye diseases, periodontitis, osteoporosis, rheumatoid arthritis, ulcerative colitis, inflammatory disorders, tumor growth and invasion (Stetler-Stevenson et al., *Annu. Rev. Cell Biol.* 1993, 9:541-73; Tryggvason et al., *Biochim. Biophys. Acta* 1987, 907:191-217; Li et al., *Mol. Carcinog.* 1998, 22:84-89),metastasis, acute lung injury, stroke, ischemia, diabetes, aortic or vascular aneurysms, skin tissue wounds, dry eye, bone and cartilage degradation (Greenwald et al., *Bone* 1998, 22:33-38; Ryan et al., *Curr. Op. Rheumatol.* 1996, 8;238-247). Other MMPAS include those described in U.S. Pat. Nos. 5,459,135; 5,321,017; 5,308,839; 5,258,371; 4,935,412; 4,704,383, 4,666,897, and RE 34,656, incorporated herein by reference in their entirety.

In another embodiment, the tetracycline compound responsive state is cancer. Examples of cancers which the tetracycline compounds of the invention may be useful to treat include all solid tumors, i.e., carcinomas e.g., adenocarcinomas, and sarcomas. Adenocarcinomas are carcinomas derived from glandular tissue or in which the tumor cells form recognizable glandular structures. Sarcomas broadly include tumors whose cells are embedded in a fibrillar or homogeneous substance like embryonic connective tissue. Examples of carcinomas which may be treated using the methods of the invention include, but are not limited to, carcinomas of the prostate, breast, ovary, testis, lung, colon, and breast. The methods of the invention are not limited to the treatment of these tumor types, but extend to any solid tumor derived from any organ system. Examples of treatable cancers include, but are not limited to, colon cancer, bladder cancer, breast cancer, melanoma, ovarian carcinoma, prostatic carcinoma, lung cancer, and a variety of other cancers as well. The methods of the invention also cause the inhibition of cancer growth in adenocarcinomas, such as, for example, those of the prostate, breast, kidney, ovary, testes, and colon.

In an embodiment, the tetracycline responsive state of the invention is cancer. The invention pertains to a method for treating a subject suffering or at risk of suffering from cancer, by administering an effective amount of a substituted tetracycline compound, such that inhibition cancer cell growth occurs, i.e., cellular proliferation, invasiveness, metastasis, or tumor incidence is decreased, slowed, or stopped. The inhibition may result from inhibition of an inflammatory process, down-regulation of an inflammatory process, some other mechanism, or a combination of mechanisms. Alternatively, the tetracycline compounds may be useful for preventing cancer recurrence, for example, to treat residual cancer following surgical resection or radiation therapy. The tetracycline compounds useful according to the invention are especially advantageous as they are substantially non-toxic compared to other cancer treatments. In a further embodiment, the compounds of the invention are administered in combination with standard cancer therapy, such as, but not limited to, chemotherapy.

The language "in combination with" another therapeutic agent or treatment includes co-administration of the tetracycline compound and with the other therapeutic agent or treatment, administration of the tetracycline compound first, followed by the other therapeutic agent or treatment and administration of the other therapeutic agent or treatment first, followed by the tetracycline compound. The other therapeutic agent may be any agent which is known in the art to treat, prevent, or reduce the symptoms of a tetracycline responsive state. Furthermore, the other therapeutic agent may be any agent of benefit to the patient when administered in combination with the administration of an tetracycline compound. In one embodiment, the cancers treated by methods of the invention include those described in U.S. Pat. Nos. 6,100,248; 5,843,925; 5,837,696; or 5,668,122, incorporated herein by reference in their entirety.

In another embodiment, the tetracycline compound responsive state is diabetes, e.g., juvenile diabetes, diabetes mellitus, diabetes type I, diabetes type II, diabetic ulcers, or other diabetic complications. In a further embodiment, protein glycosylation is not affected by the administration of the tetracycline compounds of the invention. In another embodiment, the tetracycline compound of the invention is administered in combination with standard diabetic therapies, such as, but not limited to insulin therapy. In a further embodiment, the IPAS includes disorders described in U.S. Pat. Nos. 5,929,055; and 5,532,227, incorporated herein by reference in their entirety.

In another embodiment, the tetracycline compound responsive state is a bone mass disorder. Bone mass disorders include disorders where a subjects bones are disorders and states where the formation, repair or remodeling of bone is advantageous. For examples bone mass disorders include osteoporosis (e.g., a decrease in bone strength and density), bone fractures, bone formation associated with surgical procedures (e.g., facial reconstruction), osteogenesis imperfecta (brittle bone disease), hypophosphatasia, Paget's disease, fibrous dysplasia, osteopetrosis, myeloma bone disease, and the depletion of calcium in bone, such as that which is related to primary hyperparathyroidism. Bone mass disorders include all states in which the formation, repair or remodeling of bone is advantageous to the subject as well as all other disorders associated with the bones or skeletal system of a subject which can be treated with the tetracycline compounds of the invention. In a further embodiment, the bone mass disorders include those described in U.S. Pat. Nos. 5,459,135; 5,231,017; 5,998,390; 5,770,588; RE 34,656; 5,308,839; 4,925,833; 3,304,227; and 4,666,897, each of which is hereby incorporated herein by reference in its entirety.

In another embodiment, the tetracycline compound responsive state is acute lung injury. Acute lung injuries include adult respiratory distress syndrome (ARDS), post-pump syndrome (PPS), and trauma. Trauma includes any injury to living tissue caused by an extrinsic agent or event. Examples of trauma include, but are not limited to, crush injuries, contact with a hard surface, or cutting or other damage to the lungs.

The invention also pertains to a method for treating acute lung injury by administering a tetracycline compound of the invention.

The tetracycline responsive states of the invention also include chronic lung disorders. The invention pertains to methods for treating chronic lung disorders by administering a tetracycline compound, such as those described herein. The method includes administering to a subject an effective amount of a substituted tetracycline compound such that the chronic lung disorder is treated. Examples of chronic lung disorders include, but are not limited, to asthma, cystic fibrosis, and emphysema. In a further embodiment, the tetracycline compounds of the invention used to treat acute and/or chronic lung disorders such as those described in U.S. Pat. Nos. 5,977,091; 6,043,231; 5,523,297; and 5,773,430, each of which is hereby incorporated herein by reference in its entirety.

In yet another embodiment, the tetracycline compound responsive state is ischemia, stroke, or ischemic stroke. The invention also pertains to a method for treating ischemia, stroke, or ischemic stroke by administering an effective amount of a substituted tetracycline compound of the invention. In a further embodiment, the compounds of the invention are used to treat such disorders as described in U.S. Pat. No. 6,231,894; 5,773,430; 5,919,775 or 5,789,395, incorporated herein by reference.

In another embodiment, the tetracycline compound responsive state is a skin wound. The invention also pertains, at least in part, to a method for improving the healing response of the epithelialized tissue (e.g., skin, mucosae) to acute traumatic injury (e.g., cut, burn, scrape, etc.). The method may include using a tetracycline compound of the invention (which may or may not have antibacterial activity) to improve the capacity of the epithelialized tissue to heal acute wounds. The method may increase the rate of collagen accumulation of the healing tissue. The method may also decrease the proteolytic activity in the epthithelialized tissue by decreasing the collagenolytic and/or gelatinolytic activity of MMPs. In a further embodiment, the tetracycline compound of the invention is administered to the surface of the skin (e.g., topically). In a further embodiment, the tetracycline compound of the invention is used to treat a skin wound, and other such disorders as described in, for example, U.S. Pat. Nos. 5,827,840; 4,704,383; 4,935,412; 5,258,371; 5,308,8391 5,459,135; 5,532,227; and 6,015,804; each of which is incorporated herein by reference in its entirety.

Examples of tetracycline responsive states also include neurological disorders which include both neuropsychiatric and neurodegenerative disorders, but are not limited to, such as Alzheimer's disease, dementias related to Alzheimer's disease (such as Pick's disease), Parkinson's and other Lewy diffuse body diseases, senile dementia, Huntington's disease, Gilles de la Tourette's syndrome, multiple sclerosis, amyotrophic lateral sclerosis (ALS), progressive supranuclear palsy, epilepsy, and Creutzfeldt-Jakob disease; autonomic function disorders such as hypertension and sleep disorders, and neuropsychiatric disorders, such as depression, schizophrenia, schizoaffective disorder, Korsakoff's psychosis, mania, anxiety disorders, or phobic disorders; learning or memory disorders, e.g., amnesia or age-related memory loss, attention deficit disorder, dysthymic disorder, major depressive disorder, mania, obsessive-compulsive disorder, psychoactive substance use disorders, anxiety, phobias, panic disorder, as well as bipolar affective disorder, e.g., severe bipolar affective (mood) disorder (BP-1), bipolar affective neurological disorders, e.g., migraine and obesity. Further neurological disorders include, for example, those listed in the American Psychiatric Association's Diagnostic and Statistical manual of Mental Disorders (DSM), the most current version of which is incorporated herein by reference in its entirety.

In yet another embodiment, the tetracycline compound responsive state is an aortic or vascular aneurysm in vascular tissue of a subject (e.g., a subject having or at risk of having an aortic or vascular aneurysm, etc.). The tetracycline compound may by effective to reduce the size of the vascular aneurysm or it may be administered to the subject prior to the onset of the vascular aneurysm such that the aneurysm is prevented. In one embodiment, the vascular tissue is an artery, e.g., the aorta, e.g., the abdominal aorta. In a further embodiment, the tetracycline compounds of the invention are used to treat disorders described in U.S. Pat. Nos. 6,043,225 and 5,834,449, incorporated herein by reference in their entirety.

Bacterial infections may be caused by a wide variety of gram positive and gram negative bacteria. The compounds of the invention are useful as antibiotics against organisms which are resistant to other tetracycline compounds. The antibiotic activity of the tetracycline compounds of the invention may be determined using the method discussed in Example 2, or by using the in vitro standard broth dilution method described in Waitz, J. A., National Commission for Clinical Laboratory Standards, Document M7-A2, vol. 10, no. 8, pp. 13-20, $2^{nd}$ edition, Villanova, Pa. (1990).

The tetracycline compounds of the invention may also be used to treat infections traditionally treated with tetracycline compounds such as, for example, rickettsiae; a number of gram-positive and gram-negative bacteria; and the agents responsible for lymphogranuloma venereum, inclusion conjunctivitis, psittacosis. The tetracycline compounds may be used to treat infections of, e.g., K. pneumoniae, Salmonella, E. hirae, A. baumanii, B. catarrhalis, H. influenzae, P. aeruginosa, E. faecium, E. coli, S. aureus or E. faecalis. In one embodiment, the tetracycline compound is used to treat a bacterial infection that is resistant to other tetracycline antibiotic compounds. The tetracycline compound of the invention may be administered with a pharmaceutically acceptable carrier.

The language "effective amount" of the compound is that amount necessary or sufficient to treat or prevent a tetracycline compound responsive state. The effective amount can vary depending on such factors as the size and weight of the subject, the type of illness, or the particular compound. For example, the choice of the compound can affect what constitutes an "effective amount". One of ordinary skill in the art would be able to study the aforementioned factors and make the determination regarding the effective amount of the tetracycline compound without undue experimentation.

The invention also pertains to methods of treatment against microorganism infections and associated diseases. The methods include administration of an effective amount of one or more minocycline compounds to a subject. The subject can be either a plant or, advantageously, an animal, e.g., a mammal, e.g., a human.

In the therapeutic methods of the invention, one or more minocycline compounds of the invention may be administered alone to a subject, or more typically a compound of the invention will be administered as part of a pharmaceutical composition in mixture with conventional excipient, i.e., pharmaceutically acceptable organic or inorganic carrier substances suitable for parenteral, oral or other desired administration and which do not deleteriously react with the active compounds and are not deleterious to the recipient thereof.

The invention also pertains to pharmaceutical compositions comprising a therapeutically effective amount of a minocycline compound and, optionally, a pharmaceutically acceptable carrier.

The language "pharmaceutically acceptable carrier" includes substances capable of being coadministered with the minocycline compound(s), and which allow both to perform their intended function, e.g., treat or prevent a tetracycline responsive state. Suitable pharmaceutically acceptable carriers include but are not limited to water, salt solutions, alcohol, vegetable oils, polyethylene glycols, gelatin, lactose, amylose, magnesium stearate, talc, silicic acid, viscous paraffin, perfume oil, fatty acid monoglycerides and diglycerides, petroethral fatty acid esters, hydroxymethyl-cellulose, polyvinylpyrrolidone, etc. The pharmaceutical preparations can be sterilized and if desired mixed with auxiliary agents, e.g., lubricants, preservatives, stabilizers, wetting agents, emulsifiers, salts for influencing osmotic pressure, buffers, colorings, flavorings and/or aromatic substances and the like which do not deleteriously react with the active compounds of the invention.

The minocycline compounds of the invention that are basic in nature are capable of forming a wide variety of salts with various inorganic and organic acids. The acids that may be used to prepare pharmaceutically acceptable acid addition salts of the minocycline compounds of the invention that are basic in nature are those that form non-toxic acid addition salts, i.e., salts containing pharmaceutically acceptable anions, such as the hydrochloride, hydrobromide, hydroiodide, nitrate, sulfate, bisulfate, phosphate, acid phosphate, isonicotinate, acetate, lactate, salicylate, citrate, acid citrate, tartrate, pantothenate, bitartrate, ascorbate, succinate, maleate, gentisinate, fumarate, gluconate, glucaronate, saccharate, formate, benzoate, glutamate, methanesulfonate, ethanesulfonate, benzenesulfonate, p-toluenesulfonate and palmoate [i.e., 1,1'-methylene-bis-(2-hydroxy-3-naphthoate)] salts. Although such salts must be pharmaceutically acceptable for administration to a subject, e.g., a mammal, it is often desirable in practice to initially isolate a minocycline compound of the invention from the reaction mixture as a pharmaceutically unacceptable salt and then simply convert the latter back to the free base compound by treatment with an alkaline reagent and subsequently convert the latter free base to a pharmaceutically acceptable acid addition salt. The acid addition salts of the base compounds of this invention are readily prepared by treating the base compound with a substantially equivalent amount of the chosen mineral or organic acid in an aqueous solvent medium or in a suitable organic solvent, such as methanol or ethanol. Upon careful evaporation of the solvent, the desired solid salt is readily obtained. The preparation of other minocycline compounds of the invention not specifically described in the foregoing experimental section can be accomplished using combinations of the reactions described above that will be apparent to those skilled in the art.

The preparation of other minocycline compounds of the invention not specifically described in the foregoing experimental section can be accomplished using combinations of the reactions described above that will be apparent to those skilled in the art.

The minocycline compounds of the invention that are acidic in nature are capable of forming a wide variety of base salts. The chemical bases that may be used as reagents to prepare pharmaceutically acceptable base salts of those minocycline compounds of the invention that are acidic in nature are those that form non-toxic base salts with such compounds. Such non-toxic base salts include, but are not limited to those derived from such pharmaceutically acceptable cations such as alkali metal cations (e.g., potassium and sodium) and alkaline earth metal cations (e.g., calcium and magnesium), ammonium or water-soluble amine addition salts such as N-methylglucamine-(meglumine), and the lower alkanolammonium and other base salts of pharmaceutically acceptable organic amines. The pharmaceutically acceptable base addition salts of minocycline compounds of the invention that are acidic in nature may be formed with pharmaceutically acceptable cations by conventional methods. Thus, these salts may be readily prepared by treating the minocycline compound of the invention with an aqueous solution of the desired pharmaceutically acceptable cation and evaporating the resulting solution to dryness, preferably under reduced pressure. Alternatively, a lower alkyl alcohol solution of the minocycline compound of the invention may be mixed with an alkoxide of the desired metal and the solution subsequently evaporated to dryness.

The preparation of other minocycline compounds of the invention not specifically described in the foregoing experimental section can be accomplished using combinations of the reactions described above that will be apparent to those skilled in the art.

The compounds of the invention and pharmaceutically acceptable salts thereof can be administered via either the oral, parenteral or topical routes. In general, these compounds are most desirably administered in effective dosages, depending upon the weight and condition of the subject being treated and the particular route of administration chosen. Variations may occur depending upon the species of the subject being treated and its individual response to said medicament, as well as on the type of pharmaceutical formulation chosen and the time period and interval at which such administration is carried out.

The pharmaceutical compositions of the invention may be administered alone or in combination with other known compositions for treating tetracycline responsive states in a subject, e.g., a mammal. Preferred mammals include pets (e.g. cats, dogs, ferrets, etc.), farm animals (cows, sheep, pigs, horses, goats, etc.), lab animals (rats, mice, monkeys, etc.), and primates (chimpanzees, humans, gorillas). The language "in combination with" a known composition is intended to include simultaneous administration of the composition of the invention and the known composition, administration of the composition of the invention first, followed by the known composition and administration of the known composition first, followed by the composition of the invention. Any of the therapeutically composition known in the art for treating tetracycline responsive states can be used in the methods of the invention.

The compounds of the invention may be administered alone or in combination with pharmaceutically acceptable carriers or diluents by any of the routes previously mentioned, and the administration may be carried out in single or multiple doses. For example, the novel therapeutic agents of this invention can be administered advantageously in a wide variety of different dosage forms, i.e., they may be combined with various pharmaceutically acceptable inert carriers in the form of tablets, capsules, lozenges, troches, hard candies, powders, sprays, creams, salves, suppositories, jellies, gels, pastes, lotions, ointments, aqueous suspensions, injectable solutions, elixirs, syrups, and the like. Such carriers include solid diluents or fillers, sterile aqueous media and various non-toxic organic solvents, etc. Moreover, oral pharmaceutical compositions can be suitably sweetened and/or flavored. In general, the therapeutically-effective compounds of this invention are present in such dosage forms at concentration levels ranging from about 5.0% to about 70% by weight.

For oral administration, tablets containing various excipients such as microcrystalline cellulose, sodium citrate, calcium carbonate, dicalcium phosphate and glycine may be employed along with various disintegrants such as starch (and preferably corn, potato or tapioca starch), alginic acid and certain complex silicates, together with granulation binders like polyvinylpyrrolidone, sucrose, gelatin and acacia. Additionally, lubricating agents such as magnesium stearate, sodium lauryl sulfate and talc are often very useful for tabletting purposes. Solid compositions of a similar type may also be employed as fillers in gelatin capsules; preferred materials in this connection also include lactose or milk sugar as well as high molecular weight polyethylene glycols. When aqueous suspensions and/or elixirs are desired for oral administration, the active ingredient may be combined with various sweetening or flavoring agents, coloring matter or dyes, and, if so desired, emulsifying and/or suspending agents as well, together with such diluents as water, ethanol, propylene glycol, glycerin and various like combinations thereof.

For parenteral administration (including intraperitoneal, subcutaneous, intravenous, intradermal or intramuscular injection), solutions of a therapeutic compound of the present invention in either sesame or peanut oil or in aqueous propylene glycol may be employed. The aqueous solutions should be suitably buffered (preferably pH greater than 8) if necessary and the liquid diluent first rendered isotonic. These aqueous solutions are suitable for intravenous injection purposes. The oily solutions are suitable for intraarticular, intramuscular and subcutaneous injection purposes. The preparation of all these solutions under sterile conditions is readily accomplished by standard pharmaceutical techniques well known to those skilled in the art. For parenteral application, examples of suitable preparations include solutions, preferably oily or aqueous solutions as well as suspensions, emulsions, or implants, including suppositories. Therapeutic compounds may be formulated in sterile form in multiple or single dose formats such as being dispersed in a fluid carrier such as sterile physiological saline or 5% saline dextrose solutions commonly used with injectables.

Additionally, it is also possible to administer the compounds of the present invention topically when treating inflammatory conditions of the skin. Examples of methods of topical administration include transdermal, buccal or sublingual application. For topical applications, therapeutic compounds can be suitably admixed in a pharmacologically inert topical carrier such as a gel, an ointment, a lotion or a cream. Such topical carriers include water, glycerol, alcohol, propylene glycol, fatty alcohols, triglycerides, fatty acid esters, or mineral oils. Other possible topical carriers are liquid petrolatum, isopropylpalmitate, polyethylene glycol, ethanol 95%, polyoxyethylene monolauriate 5% in water, sodium lauryl sulfate 5% in water, and the like. In addition, materials such as anti-oxidants, humectants, viscosity stabilizers and the like also may be added if desired.

For enteral application, particularly suitable are tablets, dragees or capsules having talc and/or carbohydrate carrier binder or the like, the carrier preferably being lactose and/or corn starch and/or potato starch. A syrup, elixir or the like can be used wherein a sweetened vehicle is employed. Sustained release compositions can be formulated including those wherein the active component is protected with differentially degradable coatings, e.g., by microencapsulation, multiple coatings, etc.

In addition to treatment of human subjects, the therapeutic methods of the invention also will have significant veterinary applications, e.g. for treatment of livestock such as cattle, sheep, goats, cows, swine and the like; poultry such as chickens, ducks, geese, turkeys and the like; horses; and pets such as dogs and cats. Also, the compounds of the invention may be used to treat non-animal subjects, such as plants.

It will be appreciated that the actual preferred amounts of active compounds used in a given therapy will vary according to the specific compound being utilized, the particular compositions formulated, the mode of application, the particular site of administration, etc. Optimal administration rates for a given protocol of administration can be readily ascertained by those skilled in the art using conventional dosage determination tests conducted with regard to the foregoing guidelines.

In general, compounds of the invention for treatment can be administered to a subject in dosages used in prior tetracycline therapies. See, for example, the *Physicians' Desk Reference*. For example, a suitable effective dose of one or more compounds of the invention will be in the range of from 0.01 to 100 milligrams per kilogram of body weight of recipient per day, preferably in the range of from 0.1 to 50 milligrams per kilogram body weight of recipient per day, more preferably in the range of 1 to 20 milligrams per kilogram body weight of recipient per day. The desired dose is suitably administered once daily, or several sub-doses, e.g. 2 to 5 sub-doses, are administered at appropriate intervals through the day, or other appropriate schedule.

It will also be understood that normal, conventionally known precautions will be taken regarding the administration of minocyclines generally to ensure their efficacy under normal use circumstances. Especially when employed for therapeutic treatment of humans and animals in vivo, the practitioner should take all sensible precautions to avoid conventionally known contradictions and toxic effects. Thus, the conventionally recognized adverse reactions of gastrointestinal distress and inflammations, the renal toxicity, hypersensitivity reactions, changes in blood, and impairment of absorption through aluminum, calcium, and magnesium ions should be duly considered in the conventional manner.

Furthermore, the invention also pertains to the use of a compound of formula I, II, III, or otherwise described herein for the preparation of a medicament. The medicament may include a pharmaceutically acceptable carrier and the compound is an effective amount, e.g. an effective amount to treat a tetracycline responsive state.

Exemplification of the Invention

Compounds of the invention may be made as described below, with modifications to the procedure below within the skill of those of ordinary skill in the art.

EXAMPLE 1

Synthesis of 9-Aminomethyl Minocycline and Derivatives thereof

Trifluoroacetic Acid (1L) was Charged into a 2L flask under argon and minocycline. HCl (200 g, 1 eq) and N-hydroxymethylphthalimide (100 g) were added to the flask while stirring. Once the entire solid dissolved, $H_2SO_4$ (200 mL) was added to the reaction. The reaction was heated to 40-50° C. for 5-6 hours. N-hydroxymethylamine (100 g) was added portionwise. When HPLC analysis confirmed that all the starting material was converted to 2,9-bis-aminomethylphthalimidominocycline, the mixture was precipitated out of 4 L of acetone. An exotherm of 15-20° C. was observed. After 1 hour of stirring, the solid was filtered, washed with acetone (200 ml), and dried with the aid of a latex rubber dam. The solid was reslurried in a methanol (1L)/t-BME (2L) mixture and the pH was adjusted to 3 using triethylamine. The solid was filtered and washed with 50 mL of methanol. The yield was 97% of 2,9-bis-aminomethylphthalimideminocycline. 2,9-bis-aminomethylphthalimideminocycline (100 g) was suspended in 2M solution of methylamine in methanol (10 eq). The reaction was stirred at room temperature for 2-3 hours, at which point HPLC analysis confirmed total conversion of the starting material to 2,9-bis aminomethylminocycline. The reaction mixture was poured into t-BME (5 volumes), and stirred for thirty minutes. Next, the suspension was filtered and washed with t-BME (200 mL) to isolate the desired product, 2,9-bis-aminomethylminocycline. 2,9-bis-aminomethylminocycline (40 g) was slurried in 200 mL water/methanol 1/9 and the pH was adjusted to 3 by the dropwise addition of trifluoroacetic acid. The mixture was heated to 40° C. for 1-2 hours. When HPLC analysis confirmed the hydrolysis of 2,9-bis-aminomethylminocycline to 9-aminomethylminocycline, the reaction was allowed to return to room temperature and the pH was adjusted to 7 using triethylamine. Isopropyl alcohol (200 mL) was added to precipitate out the solid. The product was filtered and washed with 50 mL IPA followed by 100 mL diethyl ether and dried under reduced pressure toisolate 9-aminomethylminocycline.

9-[(Benzylamino)-methyl]-minocycline Dihydrochloride

To 1.0 mmol (600 mg) of 9-(aminomethyl)-minocycline dihydrochloride and in 5 mL of dimethylformamide was added 0.2 mmol (5 mg) of indium trichloride and 1.5 mmol (160 mg) of benzaldehyde at room temperature. After 30 minutes of shaking, 2 mmol (424 mg) of sodium triacetoxyborohydride was added and the reaction was monitored by HPLC. After 1.5 hours, 3 equivalents of triethylamine and 1 equivalent of sodium triacetoxyborohydride. The reaction was complete after 3 hours. The solvent was removed in vacuo and the crude product was purified by preparative HPLC to yield 60 mg of 9-[(benzylamino)-methyl]-minocycline dihydrochloride. LCMS (MH+)=577.

9-[(2,2, dimethyl-propyl amino)-methyl]-minocycline Dihydrochloride 9-(aminomethyl)minocycline (200 mg, 1 eq.), DMF, and trimethylacetaldehyde (45 µl, 1 eq.) were combined in 40 mL flasks and stirred. Triethylamine (150 µL, 3 eq.) was then added. After stirring at room temperature for several minutes, NaBH(OAc)$_3$ (175 mg, 2 eq.) and InCl$_3$ (9 mg, 0.1 eq.) was added. After one hour, the reactions were clear and red. Liquid chromatography showed a single product for the reaction. The reaction was quenched with methanol, the solvent was removed, and the product was purified using column chromatography.

9-[3,4-(Methylenedioxo)phenyl-ureido]-methylminocycline dihydrochloride

To 0.25 mmol (150 mg) of 9-(aminomethyl)-minocycline dihydrochloride and 2 equivalents of triethylamine in 3 mL of dimethylformamide was added 0.5 mmol (81.5 mg) of 3,4-(methylenedioxo)phenyl isocyanate at room temperature. Solution was shaken until reaction was complete (3 hours). Solvent was removed in vacuo and crude product was purified by preparative HPLC to yield 66 mg of 9-[3,4-(methylenedioxo)phenyl-ureido]-methylminocycline dihydrochloride. Yield 41%. LCMS (MH+)=650.

9-[4-(Trifluoromethoxy)phenyl-ureido]-methylminocycline dihydrochloride

To 0.25 mmol (150 mg) of 9-(aminomethyl)-minocycline dihydrochloride and 2 equivalents of triethylamine in 3 mL of dimethylformamide was added 0.5 mmol (101.5 mg) of 4-(trifluoromethoxy)phenyl isocyanate at room temperature. The solution was shaken until the reaction was complete (3 hours). Solvent was removed in vacuo and crude product was purified by preparative HPLC to yield 68 mg of 9-[4-(trifluoromethoxy)phenyl-ureido]-methylminocycline dihydrochloride. Yield 39%. LCMS (MH+)=690.

9-(2'-Phenyl-ethyl-1'-amino)-methyl]-doxycycline

Under an N$_2$ atmosphere, a stirred solution of 9-aminomethyldoxycycline dihydrochloride (1.21 g, 2.21 mmol) in DMF (10 mL), was treated with InCl$_3$ (0.076 g, 0.34 mmol) and phenylacetaldehyde (0.511 mL; 4.4 mmol). HPLC and LCMS monitoring of the reaction indicated the complete consumption of the starting material over the course of 12 hours. The products were both the mono- (major) and bis- (minor) substituted aminodoxycyclines. Methanol (10 mL) was added to quench the reaction. The reaction mixture was filtered through a bed of Celite, the celite washed with methanol (2×5 mL), and the combined organic layer was concentrated to about 7-8 mL and diluted with ether. The resulting amorphous solid was filtered, washed with ether (6×15 mL) and dried under vacuum to afford a red powder, which was purified by preparative HPLC. The final product was characterized by HPLC, MS, and $^1$H NMR spectroscopic methods. MS (m/z): Theor. 577.24; Found: 578.17 (M+1).

EXAMPLE 2

In Vitro Minimum Inhibitory Concentration (MIC) Assay

The following assay is used to determine the efficacy of compounds against common bacteria. 2 mg of each compound is dissolved in 100 µl of DMSO. The solution is then added to cation-adjusted Mueller Hinton broth (CAMHB), which results in a final compound concentration of 200 µg per ml. The compound solutions are diluted to 50 µL volumes, with a test compound concentration of 0.098 µg/ml. Optical density (OD) determinations are made from fresh log-phase broth cultures of the test strains. Dilutions are made to achieve a final cell density of 1×10$^6$ CFU/ml. At OD=1, cell densities for different genera should be approximately:

| | |
|---|---|
| E. coli | 1 × 10$^9$ CFU/ml |
| S. aureus | 5 × 10$^8$ CFU/ml |
| Enterococcus sp. | 2.5 × 10$^9$ CFU/ml |

50 µl of the cell suspensions are added to each well of microtiter plates. The final cell density should be approximately 5×10$^5$ CFU/ml. These plates are incubated at 35° C. in an ambient air incubator for approximately 18 hr. The plates are read with a microplate reader and are visually inspected when necessary. The MIC is defined as the lowest concentration of the compound that inhibits growth. Compounds of the invention indicate good inhibition of growth.

In Table 1, compounds which were good inhibitors of growth of a particular bacteria are indicated with *, compounds which were very good inhibitors of a particular bacteria are indicated with , and compounds with were particularly good inhibitors of a particular bacteria are indicated with *.

Equivalents

Those skilled in the art will recognize, or be able to ascertain using no more than routine experimentation, numerous equivalents to the specific procedures described herein. S Such equivalents are considered to be within the scope of the present invention and are covered by the following claims. The contents of all references, patents, and patent applications cited throughout this application are hereby incorporated by reference. The appropriate components, processes, and methods of those patents, applications and other documents may be selected for the present invention and embodiments thereof.

| ID | STRUCTURE | S. aureus | E. hirae | E. coli |
|---|---|---|---|---|
| NZ | 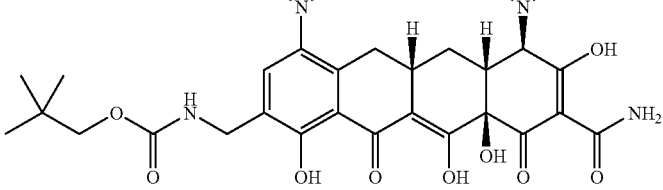 |  |  | * |
| OA | 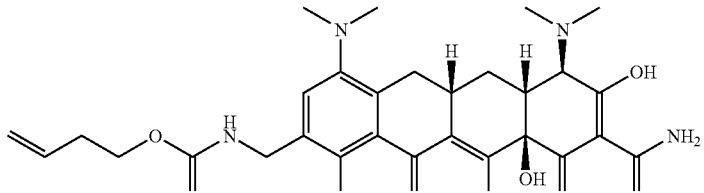 |  |  | * |
| OB | 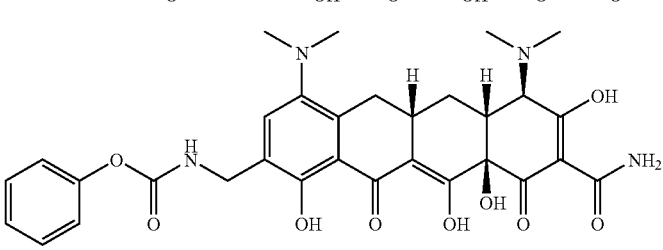 |  |  | * |
| OD | 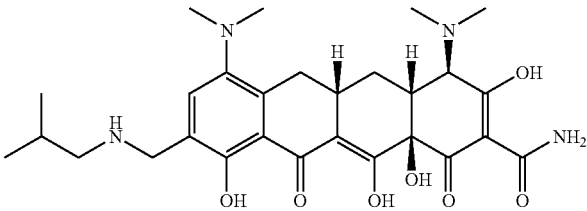 |  | NT | * |
| OG | 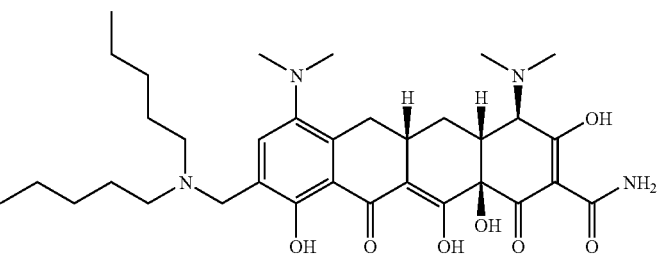 |  | NT |  |
| OH | 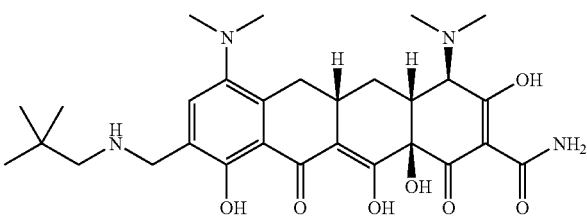 | * | NT | * |
| OK | 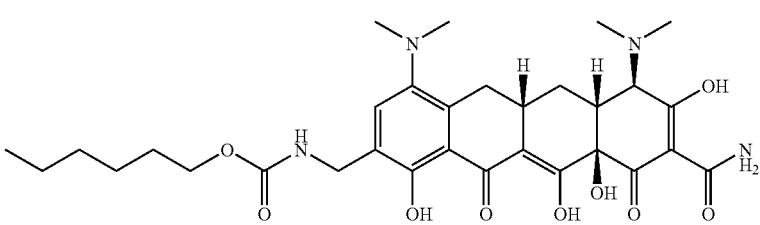 |  | NT |  |

| ID | STRUCTURE | S. aureus | E. hirae | E. coli |
|---|---|---|---|---|
| OL | 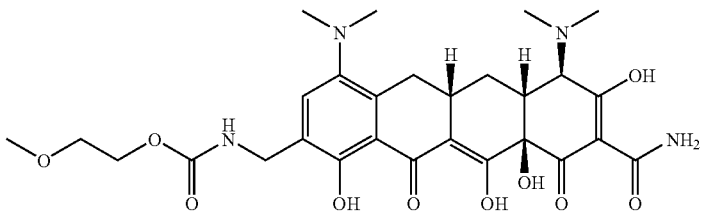 | * | NT | * |
| OM | 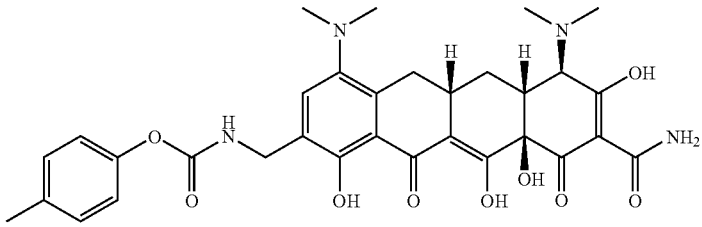 | ** | NT | * |
| ON | 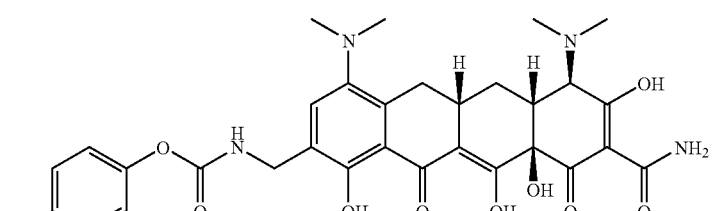 | ** | NT | * |
| OO | 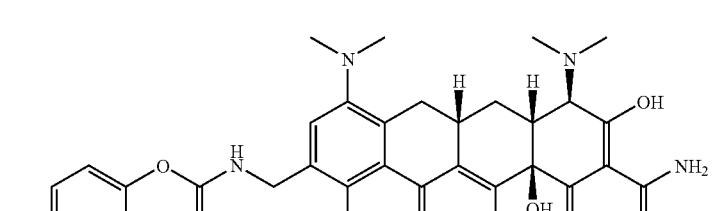 |  | NT |  |
| OP | 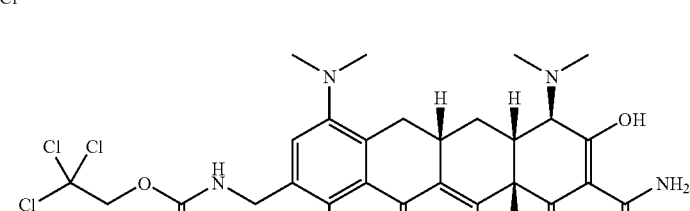 |  | NT |  |
| OQ | 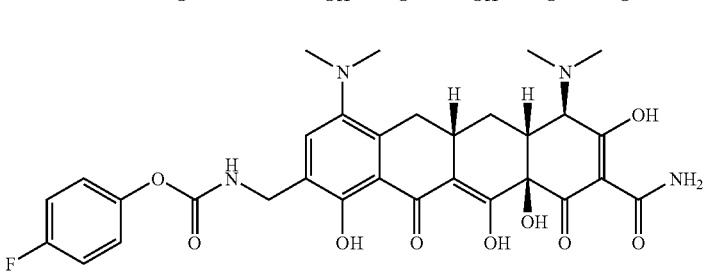 | ** | NT | * |

| ID | STRUCTURE | S. aureus | E. hirae | E. coli |
|---|---|---|---|---|
| OR | 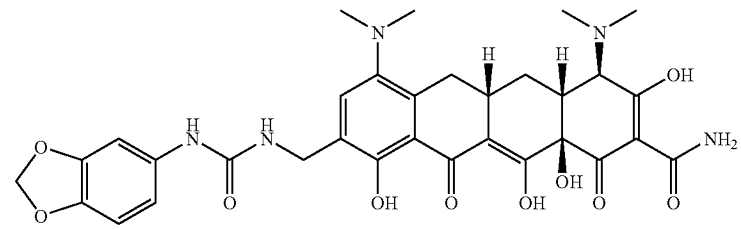 | * | NT | 8 |
| OS | 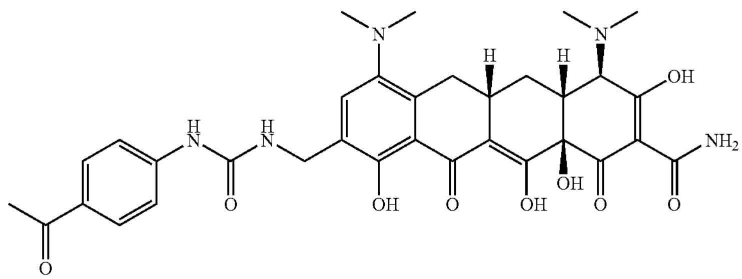 | * | NT | 8 |
| OT | 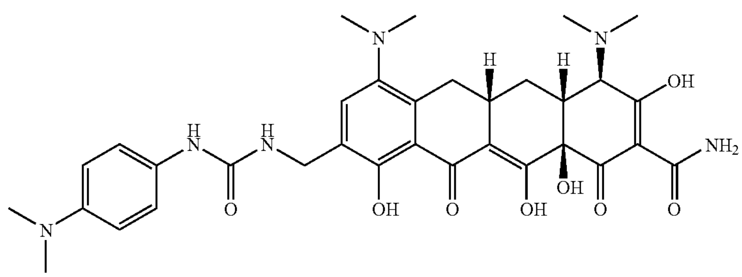 | * | NT | * |
| OU | 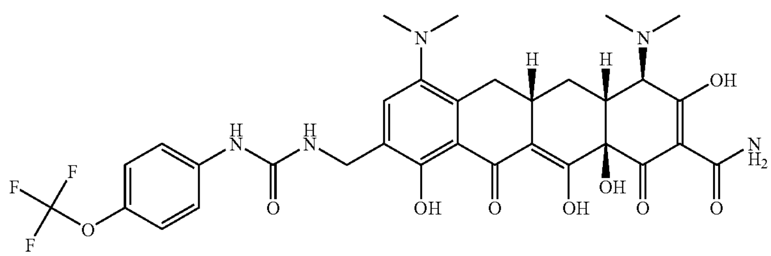 | ** | NT | * |
| OV | 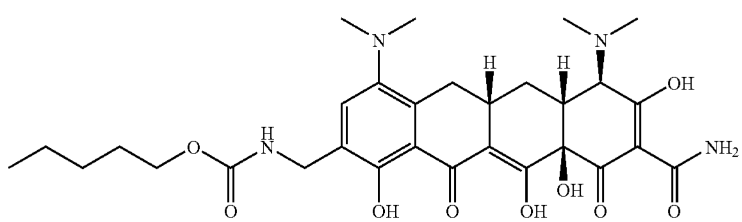 |  | NT |  |
| PE | 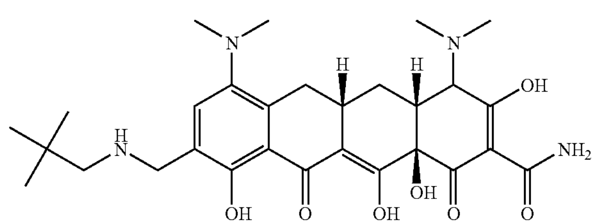 | NT | NT | NT |

-continued
| ID | STRUCTURE | S. aureus | E. hirae | E. coli |
|---|---|---|---|---|
| PM | 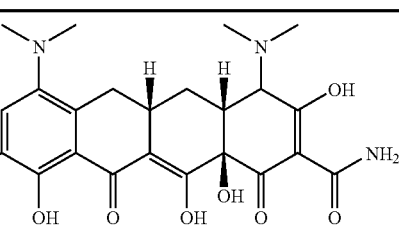 | NT | NT | NT |
| PQ | 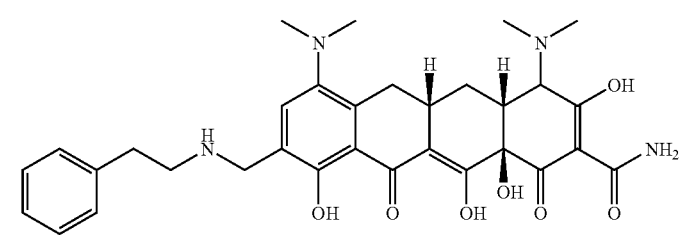 | NT | NT | NT |
| PR | 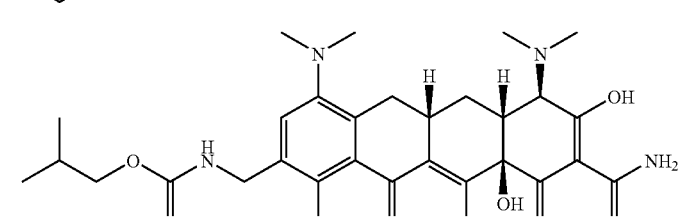 | NT | NT | NT |
| PS | 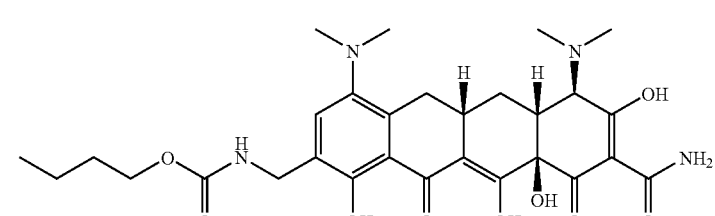 | NT | NT | NT |
| PT | 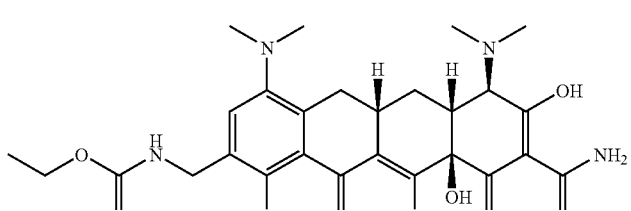 | NT | NT | NT |
| PV | 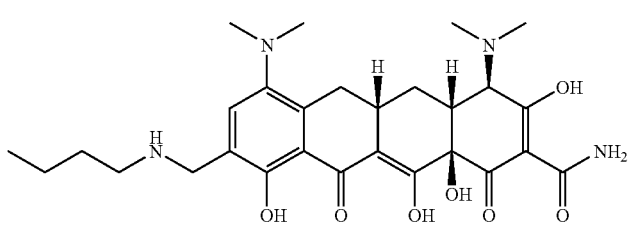 | NT | NT | NT |
| PW | 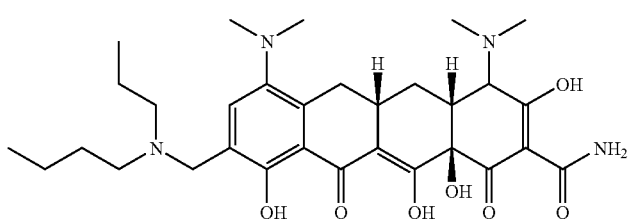 | NT | NT | NT |

The invention claimed is:
1. A compound of the formula:

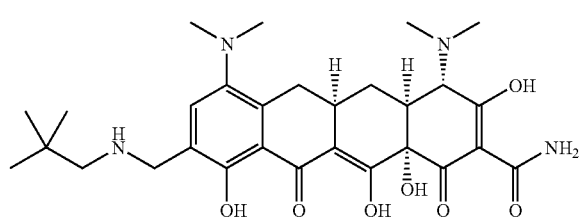

or a pharmaceutically acceptable salt or ester thereof.

2. A compound of the formula:

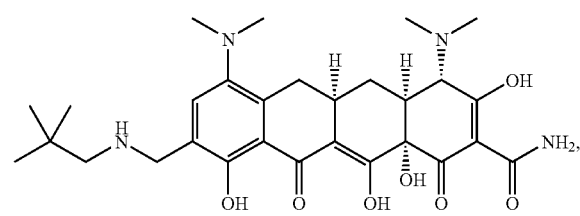

or a pharmaceutically acceptable salt thereof.

3. A compound of the formula:

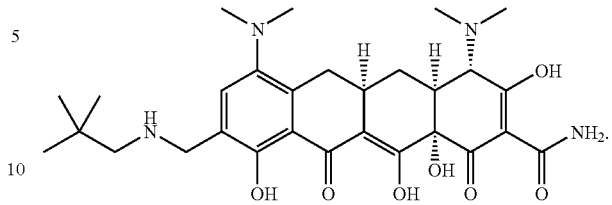

4. A pharmaceutical composition comprising a therapeutically effective amount of a compound of any one of claims 1, 2 and 3, and a pharmaceutically acceptable carrier.

* * * * *

UNITED STATES PATENT AND TRADEMARK OFFICE
CERTIFICATE OF CORRECTION

| | | |
|---|---|---|
| PATENT NO. | : 7,553,828 B2 | Page 1 of 1 |
| APPLICATION NO. | : 10/786881 | |
| DATED | : June 30, 2009 | |
| INVENTOR(S) | : Nelson et al. | |

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 703 days.

Signed and Sealed this
Seventh Day of August, 2012

David J. Kappos
*Director of the United States Patent and Trademark Office*